US011833255B2

(12) United States Patent
Chopra et al.

(10) Patent No.: US 11,833,255 B2
(45) Date of Patent: Dec. 5, 2023

(54) NANOPARTICLES WITH PH TRIGGERED DRUG RELEASE

(71) Applicants: The Brigham and Women's Hospital, Inc., Boston, MA (US); MASSACHUSETTS INSTITUTE OF TECHNOLOGY, Cambridge, MA (US)

(72) Inventors: Sunandini Chopra, Cambridge, MA (US); Rohit Karnik, Cambridge, MA (US); Amy Wang, Cambridge, MA (US); Omid C. Farokhzad, Waban, MA (US); Xue-Qing Zhang, Livingston, NJ (US)

(73) Assignees: The Brigham and Women's Hospital, Inc., Boston, MA (US); Massachusetts Institute Of Technology, Cambridge, MA (US)

( * ) Notice: Subject to any disclaimer, the term of this patent is extended or adjusted under 35 U.S.C. 154(b) by 29 days.

(21) Appl. No.: 15/766,706

(22) PCT Filed: Oct. 7, 2016

(86) PCT No.: PCT/US2016/056193
§ 371 (c)(1),
(2) Date: Apr. 6, 2018

(87) PCT Pub. No.: WO2017/062920
PCT Pub. Date: Apr. 13, 2017

(65) Prior Publication Data
US 2018/0318230 A1  Nov. 8, 2018

Related U.S. Application Data

(60) Provisional application No. 62/238,239, filed on Oct. 7, 2015.

(51) Int. Cl.
| | |
|---|---|
| *A61K 9/51* | (2006.01) |
| *A61K 9/00* | (2006.01) |
| *A61K 47/69* | (2017.01) |
| *A61K 47/68* | (2017.01) |
| *A61P 3/10* | (2006.01) |
| *A61P 35/00* | (2006.01) |
| *A61K 38/28* | (2006.01) |

(52) U.S. Cl.
CPC .......... *A61K 9/5153* (2013.01); *A61K 9/0019* (2013.01); *A61K 9/5138* (2013.01); *A61K 9/5146* (2013.01); *A61K 38/28* (2013.01); *A61K 47/6803* (2017.08); *A61K 47/6933* (2017.08); *A61K 47/6937* (2017.08); *A61P 3/10* (2018.01); *A61P 35/00* (2018.01); *Y02A 50/30* (2018.01)

(58) Field of Classification Search
CPC .. A61K 9/5153; A61K 9/5146; A61K 9/0019; A61K 47/6933; A61K 47/6937; A61K 47/6803; A61K 38/28; A61K 9/5138; A61P 3/10; A61P 35/00; Y02A 50/475; Y02A 50/401; Y02A 50/481
See application file for complete search history.

(56) References Cited

U.S. PATENT DOCUMENTS

| | | | |
|---|---|---|---|
| 2010/0266692 A1 | 10/2010 | Bloom et al. | |
| 2010/0284965 A1 | 11/2010 | Fahmy et al. | |
| 2012/0231069 A1* | 9/2012 | Nowotnik | B82Y 5/00 424/450 |
| 2013/0034589 A1 | 2/2013 | Zhang et al. | |
| 2015/0125384 A1 | 5/2015 | Mellman et al. | |
| 2015/0174225 A1 | 6/2015 | Caplan | |
| 2015/0258102 A1* | 9/2015 | Bagrodia | A61K 47/12 544/83 |

FOREIGN PATENT DOCUMENTS

| | | | |
|---|---|---|---|
| WO | WO 2007/150030 | 12/2007 | |
| WO | WO-2009073216 A1 * | 6/2009 | ........... A61K 9/0048 |

OTHER PUBLICATIONS

Dillen et al. ("Evaluation of ciprofloxacin-loaded Eudragit RS100 or RL100/PLGA nanoparticles". Int J Pharm. May 11, 2006;314(1): 72-82) (Year: 2006).*
International Search Report and Written Opinion dated Dec. 27, 2016 in international application No. PCT/US2016/056193, 12 pgs.
Balashanmugam et al., "Preparation and Characterization of Novel PBAE/PLGA Polymer Blend Microparticles for DNA Vaccine Delivery", The Scientific World Journal, 2014: 1-3 (Oct. 2014).
Cetin et al., "Salmon calcitonin-loaded Eudragit and Eudragit-PLGA nanoparticles: in vitro and in vivo evaluation", Journal of Microencapsulation, 29(2): 156-166 (2012).
Cui et al., "Preparation of Insulin Loaded PLGA-Hp55 Nanoparticles for Oral Delivery", J. Pharmaceutical Sci. 96 (2): 421-427 (Feb. 2007).
Gao, "pH-Responsive nanoparticles for drug delivery," Mol. Pharmaceuticals, 2010, 7, 1913-1920.
International Preliminary Report on Patentability in International Application No. PCT/US2016/056193, dated Apr. 10, 2018, 7 pages.
Pridgen et al., "Transepithelial transport of Fc-targeted nanoparticles by the neonatal fc receptor for oral delivery," Science Translational Medicine, 2013, 5(213): 213ra167.
Taluja et al., "Novel approaches in microparticulate PLGA delivery systems encapsulating proteins," J. Mat. Chem, 2007, 17: 4002-4014.

* cited by examiner

*Primary Examiner* — Robert A Wax
*Assistant Examiner* — Quanglong N Truong
(74) *Attorney, Agent, or Firm* — Fish & Richardson P.C.

(57) ABSTRACT

Provided is a nanoparticle comprising a pH-responsive polymer, a pH-insensitive polymer and a payload molecule. The nanoparticle can act as a system for delivery of the payload that releases the payload in a pH sensitive manner.

16 Claims, 7 Drawing Sheets

Eudragit S100
Poly (MA-MMA) – Ratio 1:2
Dissolution pH > 7

Eudragit L100
Poly (MA-MMA) – Ratio 1:1
Dissolution pH > 6

NANOPARTICLES WITH PH TRIGGERED DRUG RELEASE

STATEMENT AS TO FEDERALLY SPONSORED RESEARCH

This invention was made with Government support under Grant Nos. EB015419 and CA151884, awarded by the National Institutes of Health. The Government has certain rights in the invention.

CROSS-REFERENCE TO RELATED APPLICATIONS

This application is a § 371 National Stage Application of PCT/US2016/056193, filed Oct. 7, 2016, which claims the benefit of U.S. Provisional Application No. 62/238,239 filed Oct. 7, 2015, which is incorporated herein by reference in its entirety.

TECHNICAL FIELD

The present invention generally relates to particles, such as nanoparticles, the polymers of which the particles are comprised, as well as to compositions thereof. The present invention also generally relates to methods of using the compositions provided for delivery of agents, such as one or more pharmaceutical agents (e.g., one or more drugs). More specifically, the present invention relates to particles such as nanoparticles that release drugs in a pH sensitive manner.

BACKGROUND

Currently some pharmaceuticals such as biologics and nanoparticle (NP)-based therapies are administered primarily via intravenous or subcutaneous injections For diseases, which require frequent doses over prolonged periods, such methods of drug administration result in patient incompliance and inconvenience. In these cases, the most preferred way of drug delivery would be oral delivery. Although oral delivery of small molecule drugs is less challenging, oral delivery of protein drugs—e.g. insulin—present several challenges. The major challenges are: (1) to make the drug and the NP to survive the changes in pH in the complex environment of the gastrointestinal tract, and (2) to release majority of the drug before the NP gets excreted by the body. Gao, W., *Mol. Pharmaceuticals,* 2010, 7, 1913-1920.

Some pharmaceuticals, however, are sensitive to conditions found in the gastrointestinal tract such as wide fluctuations in pH and enzyme activity. For example therapeutic biologics include large protein molecules like insulin, calcitonin etc. Their large size, and sensitivity to the complex gastrointestinal environment with of a wide range of pH and enzyme activity, makes it challenging to deliver these biologics orally. Moreover, many transport pathways, like the FcRn pathway that enable the transcytosis of NPs across the intestinal epithelium to blood, work efficiently for small size NPs. Pridgen, et al., Transepithelial transport of Fc-targeted nanoparticles by the neonatal fc receptor for oral delivery. *Science Translational medicine,* 2013, 5(213), 213ra167. Once the NPs cross the intestinal epithelium they are susceptible to clearance by the mononuclear phagocyte system. This problem is exacerbated in the case of FcRn-targeted NPs that are decorated with Fc fragments that enhance clearance of the NPs.

Rapid release of the payload after transcytosis of NPs into the blood stream might one way of addressing the problem of delivering sensitive drugs to the body. The drug could be released rapidly before the NPs are cleared (other ways are to shed targeting ligand (Fc) or to entirely dissolve the NP upon transcytosis into the bloodstream). Therefore, the main challenges associated with making NPs which can efficiently deliver large protein molecules across the intestinal epithelium would be: (1) to ensure that the NP diameter is sufficiently small (e.g., less than about 100 nm); (2) to ensure that the NP has a loading of the drug (e.g., a therapeutic protein); (3) to make the drug and the NP survive the changes in pH in the complex environment of the gastrointestinal tract, and (4) to trigger quick release of majority of the drug before the NP is excreted from the body (or to shed targeting ligand. or dissolve the NP).

The present disclosure provides pH-responsive NPs and methods of making them that address these challenges.

SUMMARY

The present disclosure provides nanoparticle comprising a pH-responsive polymer, a pH-insensitive polymer and a payload molecule.

In some embodiments, the pH-responsive polymer is blended with the pH-insensitive polymer forming a mixture of the polymers.

In some embodiments, the pH-insensitive polymer is a water-insoluble polymer, the aqueous solubility of which does not substantially vary with pH.

In some embodiments, the pH-insensitive polymer is a hydrophobic polymer.

In some embodiments, the pH-insensitive polymer is selected from the group consisting of polylactic acid (PLA), polypropylene oxide, poly(lactide-co-glycolide) (PLGA), poly(lactide-co-glycolide)polyethylene glycol copolymer (PLGA-PEG), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, a polymer of any of the following: methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole) and styrenes, and combinations thereof.

In some embodiments, the pH-insensitive polymer is poly(lactide-co-glycolide)polyethylene glycol copolymer (PLGA-PEG).

In some embodiments, the pH-sensitive polymer is a polymer, the aqueous solubility of which varies from being substantially insoluble to being substantially soluble with changes in pH.

In some embodiments, the pH-sensitive polymer is a polymer containing acidic groups.

In some embodiments, the pH-sensitive polymer is a polymer containing carboxylic acid groups.

In some embodiments, the aqueous solubility of the pH-sensitive polymer varies from being substantially insoluble at acidic pH to being substantially soluble at basic pH.

In some embodiments, the pH-sensitive polymer is a polymer containing basic groups.

In some embodiments, the pH-sensitive polymer is a polymer containing amine groups.

In some embodiments, the pH-sensitive polymer is a polymer containing amino groups ($NH_2$), alkylamine groups, and/or dialkylamine groups.

In some embodiments, the aqueous solubility of the pH-sensitive polymer varies from being substantially insoluble at basic pH to being substantially soluble at acidic pH.

In some embodiments, the pH-sensitive polymer is selected from the group consisting of polyacrylic acid, polymethacrylic acid, copolymers of acrylic acid and acrylates or methacrylates, and copolymers of methacrylic acid and acrylates or methacrylates.

In some embodiments, the pH-sensitive polymer is selected from the group consisting of acrylic acid-isooctyl acrylate copolymer; ammonio methacrylate copolymer O; ammonio methacrylate copolymer type A O; ammonio methacrylate copolymer type B O; dimethylaminoethyl methacrylate-butyl methacrylate-methyl methacrylate copolymer O; methacrylic acid-ethyl acrylate copolymer (1:1) type A O; methacrylic acid-methyl methacrylate copolymer (1:1) O; methacrylic acid-methyl methacrylate copolymer (1:2) O; methacrylic acid copolymer O; methacrylic acid copolymer type A O; methacrylic acid copolymer type B O; methacrylic acid copolymer type C O; aminoalkylacrylates, aminoalkylmethacrylates, aminoalkyl(meth)acrylamides).

In some embodiments, the pH-sensitive polymer is a methacrylic acid methyl methacrylate copolymer.

In some embodiments, the pH-sensitive polymer is selected from the group consisting of methacrylic acid-methyl methacrylate copolymer (1:1) and methacrylic acid-methyl methacrylate copolymer (1:2).

In some embodiments, the pH-sensitive polymer is selected from the group consisting of EUDRAGIT® L100 and EUDRAGIT® S100.

In some embodiments, the ratio of the amount of the pH-sensitive polymer to the amount of pH-insensitive polymer is in the range from about 1:99 to about 50:50 by weight.

In some embodiments, the ratio of the amount of the pH-sensitive polymer to the amount of pH-insensitive polymer is in the range from about 1:99 to about 30:70 by weight.

In some embodiments, the ratio of the amount of the pH-sensitive polymer to the amount of pH-insensitive polymer is in the range from about 1:99 to about 20:80 by weight.

In some embodiments, the ratio of the amount of the pH-sensitive polymer to the amount of pH-insensitive polymer is in the range from about 5:95 to about 20:80 by weight.

In some embodiments, the ratio of the amount of the pH-sensitive polymer to the amount of pH-insensitive polymer is in the range from about 10:90 to about 20:80 by weight.

In some embodiments, the size of the nanoparticle is in the range from about 5 nm to about 500 nm.

In some embodiments, the size of the nanoparticle is in the range from about 5 nm to about 200 nm.

In some embodiments, the size of the nanoparticle is in the range from about 10 nm to about 100 nm.

In some embodiments, the size of the nanoparticle is in the range from about 20 nm to about 100 nm.

In some embodiments, the payload is a biomolecule.
In some embodiments, the biomolecule is a polypeptide.
In some embodiments, the biomolecule is a protein.
In some embodiments, the biomolecule is a nucleic acid.

In some embodiments, the biomolecule is selected from the group consisting of polypeptide hormones; antibody-drug conjugates; antibody fragment-drug conjugates; protein-drug conjugates; peptide-drug conjugates; fusion proteins; enzymes; monoclonal antibodies; bispecific monoclonal antibodies; and multimeric fusion proteins.

In some embodiments, the biomolecule is selected from the group consisting of: transforming growth factor-beta, interferons, colony stimulating factors, granulocyte colony stimulating factor (GM-CSF), thymic stromal lymphopoietin (TSLP), interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, interleukin-35, amylin, anti-Müllerian hormone, calcitonin, cholecystokinin, corticotropin, endothelin, enkephalin, erythropoietin (EPO), follicle-stimulating hormone, gallanin, gastrin, ghrelin, glucagon, gonadotropin-releasing hormone, growth hormone-releasing hormone, hepcidin, human chorionic gonadotropin, human growth hormone (hGH), inhibin, insulin, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, vasopressin, atacicept, abatacept, alefacept, etanercept, romiplostim, rilonacept, agalsidase beta, imiglucerase, velaglucerase alfa, taliglucerase, alglucosidase alfa, laronidase, idursulfase, and galsulfase, abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, zalutumumab, adalimumab, alemtuzumab, atlizumab, canakinumab, certolizumab, certolizumab pegol, daclizumab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, and briakinumab.

In some embodiments, the biomolecule is erythropoietin.
In some embodiments, the biomolecule is insulin.
In some embodiments, the biomolecule is human growth hormone.
In some embodiments, the biomolecule is a cytokine.
In some embodiments, the biomolecule is an interleukin.
In some embodiments, the biomolecule is interleukin-2.
In some embodiments, the biomolecule is interleukin-10.
In some embodiments, the payload is attached (e.g., conjugated) to the pH-sensitive polymer or the pH-insensitive polymer.

In some embodiments, the nanoparticle further comprises a targeting molecule.

In some embodiments, the targeting molecule is selected form the group consisting of antibodies, antibody fragments, aptamers, peptides, aptides, sugars, small molecules, and combinations thereof.

In some embodiments, the targeting molecule is an antibody.

In some embodiments, the targeting molecule is an IgG antibody.

In some embodiments, the targeting molecule comprises an Fc portion of an antibody (e.g., an IgG antibody).

In some embodiments, the targeting molecule is presented on the surface of the nanoparticle.

In some embodiments, the targeting molecule is attached (e.g., conjugated) to the pH-sensitive polymer or the pH-insensitive polymer.

In some embodiments, the targeting molecule is attached (e.g., conjugated) to the pH-sensitive polymer or the pH-insensitive polymer.

In some embodiments, there is provided a method of delivering a payload to an individual in need thereof, comprising administering to the individual an effective amount of a nanoparticle as described herein.

In some embodiments, there is provided a method of treating diabetes in a subject in need thereof, the method comprising administering to the subject a therapeutically effective amount of a nanoparticle described herein, wherein the payload is indicated for treatment of diabetes (e.g., insulin).

In some embodiments, the diabetes is type 1 diabetes.

In some embodiments, the diabetes is type 2 diabetes.

In some embodiments, there is provided a method of treating a cancer in a subject in need thereof, the method comprising administering to the subject a therapeutically effective amount of a nanoparticle described herein, wherein the payload is indicated for treatment of the cancer.

In some embodiments, there is provided a method of treating a disease or a condition in need of enzyme replacement in a subject in need thereof, the method comprising administering to the subject a therapeutically effective amount of a nanoparticle described herein, wherein the payload is indicated for treating the disease or condition in need of enzyme replacement.

In some embodiments, there is provided a method of preventing or treating a viral disease in a subject in need thereof, the method comprising administering to the subject a therapeutically effective amount of a nanoparticle described herein wherein the payload is indicated for treatment of the viral disease.

In some embodiments, there is provided a method of treating an inflammatory disease in a subject in need thereof, the method comprising administering to the subject a therapeutically effective amount of a nanoparticle described herein, wherein the payload is indicated for treatment of the inflammatory disease.

In some embodiments, the inflammatory disease or condition is selected from the group consisting of: atherosclerosis, Alzheimer's disease, arthritis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, fibromyalgia, achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, *Staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

DETAILED DESCRIPTION

Figure 1A:
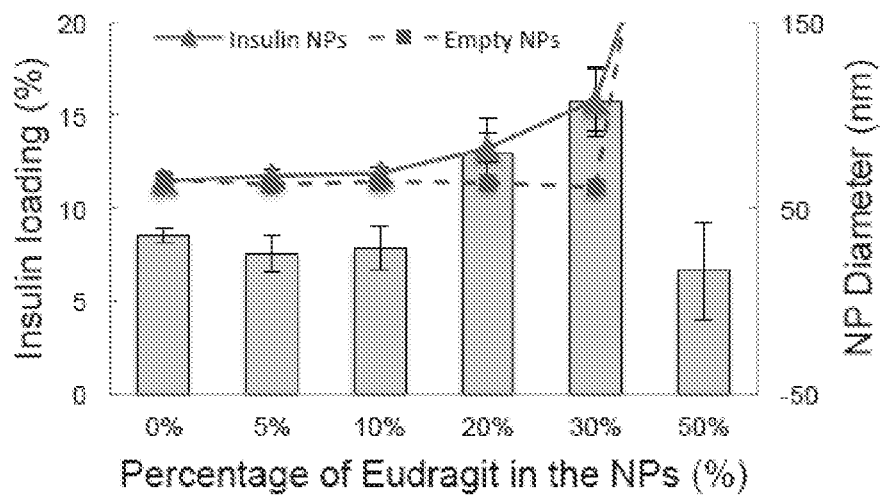
FIG. 1A is a graph showing the effect of the amount of Eudragit on NP size and insulin loading. Insulin loading increases as the amount of Eudragit increases in the NPs up to 30% by weight The NP size remains fairly constant up to 10% Eudragit by weight (~60 nm), but increases to 83 nm at 20% Eudragit, and even larger for 30% and 50% insulin.

The current application provides nanoparticles that contain pH-sensitive polymers and pH-insensitive polymers that release drug (e.g., a protein drug) in a pH-dependent manner. Such compositions can be delivered in a controlled release fashion to provide enhanced delivery of a cancer or other chemotherapeutic with an improved in vivo half-life compared to the free drug.

In the present description, it is appreciated that certain features described herein, which, for clarity, are described in the context of separate embodiments, can also be provided in combination in a single embodiment. Conversely, various features described herein which are, for brevity, described in the context of a single embodiment, can also be provided separately or in any suitable subcombination.

Although methods and materials similar or equivalent to those described herein can be used in the practice or testing of the present invention, suitable methods and materials are described below. In addition, the materials, methods and examples are illustrative only and not intended to be limiting.

I. Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

As used herein, "alkyl" refers to a saturated hydrocarbon chain that may be a straight chain or a branched chain. An alkyl group formally corresponds to an alkane with one C—H bond replaced by the point of attachment of the alkyl group. The term "$(C_{x-y})$alkyl" (wherein x and y are integers) by itself or as part of another substituent means, unless otherwise stated, an alkyl group containing from x to y carbon atoms. For example, a $(C_{1-6})$alkyl group may have from one to six (inclusive) carbon atoms in it. Examples of $(C_{1-6})$alkyl groups include, but are not limited to, methyl, ethyl, n-propyl, n-butyl, n-pentyl, n-hexyl, isopropyl, isobutyl, sec-butyl, tert-butyl, isopentyl, neopentyl and isohexyl. The $(C_{x-y})$alkyl groups include $(C_{1-6})$alkyl, $(C_{1-4})$alkyl and $(C_{1-3})$alkyl.

The term "$(C_{x-y})$alkylene" (wherein x and y are integers) refers to an alkylene group containing from x to y carbon atoms. An alkylene group formally corresponds to an alkane with two C—H bonds replaced by points of attachment of the alkylene group. Examples are divalent straight hydrocarbon groups consisting of methylene groups, such as, —$CH_2$—, —$CH_2CH_2$—, —$CH_2CH_2CH_2$—. The $(C_{x-y})$alkylene groups include $(C_{1-6})$alkylene and $(C_{1-3})$alkylene.

As used herein, "alkenyl" refers to an unsaturated hydrocarbon chain that includes a C═C double bond. An alkenyl group formally corresponds to an alkene with one C—H bond replaced by the point of attachment of the alkenyl group. The term "$(C_{x-y})$alkenyl" (wherein x and y are integers) denotes a radical containing x to y carbons, wherein at least one carbon-carbon double bond is present (therefore x must be at least 2). Some embodiments are 2 to 4 carbons, some embodiments are 2 to 3 carbons and some embodiments have 2 carbons. Alkenyl groups may include both E and Z stereoisomers. An alkenyl group can include more than one double bond. Examples of alkenyl groups include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl, and the like.

The term "$(C_{x-y})$alkenylene" (wherein x and y are integers) refers to an alkenylene group containing from x to y carbon atoms. An alkenylene group formally corresponds to an alkene with two C—H bonds replaced by points of attachment of the alkenylene group. Examples are divalent straight hydrocarbon groups consisting of alkenyl groups, such as —HC=CH— and —HC=CH—CH$_2$—. The $(C_{x-y})$alkenylene groups include $(C_{2-6})$alkenylene and $(C_{2-4})$alkenylene.

The term "$(C_{x-y})$heteroalkylene" (wherein x and y are integers) refers to a heteroalkylene group containing from x to y carbon atoms. A heteroalkylene group corresponds to an alkylene group wherein one or more of the carbon atoms have been replaced by a heteroatom. The heteroatoms may be independently selected from the group consisting of O, N and S. A divalent heteroatom (e.g., O or S) replaces a methylene group of the alkylene —CH$_2$—, and a trivalent heteroatom (e.g., N) replaces a methine group. Examples are divalent straight hydrocarbon groups consisting of methylene groups, such as, —CH$_2$—, —CH$_2$CH$_2$—, —CH$_2$CH$_2$CH$_2$—. The $(C_{x-y})$alkylene groups include $(C_{1-6})$heteroalkylene and $(C_{1-3})$heteroalkylene.

As used herein, "alkynyl" refers to an unsaturated hydrocarbon chain that includes a C≡C triple bond. An alkynyl group formally corresponds to an alkyne with one C—H bond replaced by the point of attachment of the alkyl group. The term "$(C_{x-y})$alkynyl" (wherein x and y are integers) denotes a radical containing x to y carbons, wherein at least one carbon-carbon triple bond is present (therefore x must be at least 2). Some embodiments are 2 to 4 carbons, some embodiments are 2 to 3 carbons and some embodiments have 2 carbons. Examples of an alkynyl include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "$(C_{x-y})$alkynylene" (wherein x and y are integers) refers to an alkynylene group containing from x to y carbon atoms. An alkynylene group formally corresponds to an alkyne with two C—H bonds replaced by points of attachment of the alkynylene group. Examples are divalent straight hydrocarbon groups consisting of alkynyl groups, such as —C≡C— and —C≡C—CH$_2$—. The $(C_{x-y})$alkylene groups include $(C_{2-6})$alkynylene and $(C_{2-3})$alkynylene.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like, e.g., indanyl or tetrahydronaphthyl. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., C(=O), S(=O), C(S) or S(=O)$_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 1,2,3,4-tetrahydroquinoline, dihydrobenzofuran, azetidine, azepane, diazepan (e.g., 1,4-diazepan), pyrrolidine, piperidine, piperazine, morpholine, thiomorpholine, pyran, tetrahydrofuran and di- and tetra-hydropyran.

As used herein, "halo" or "halogen" refers to —F, —Cl, —Br and —I.

As used herein, "aryl," employed alone or in combination with other terms, refers to an aromatic hydrocarbon group. The aryl group may be composed of, e.g., monocyclic or bicyclic rings and may contain, e.g., from 6 to 12 carbons in the ring, such as phenyl, biphenyl and naphthyl. The term "$(C_{x-y})$aryl" (wherein x and y are integers) denotes an aryl group containing from x to y ring carbon atoms. Examples of a $(C_{6-14})$aryl group include, but are not limited to, phenyl, α-naphthyl, β-naphthyl, biphenyl, anthryl, tetrahydronaphthyl, fluorenyl, indanyl, biphenylenyl and acenaphthyl. Examples of a $C_{6-10}$ aryl group include, but are not limited to, phenyl, α-naphthyl, β-naphthyl, biphenyl and tetrahydronaphthyl.

An aryl group can be unsubstituted or substituted. A substituted aryl group can be substituted with one or more groups, e.g., 1, 2 or 3 groups, including: $(C_{1-6})$alkyl, $(C_{2-6})$alkenyl, $(C_{2-6})$alkynyl, halogen, $(C_{1-6})$haloalkyl, —CN, —NO$_2$, —C(=O)R, —C(=O)OR, —C(=O)NR$_2$, —C(=NR)NR$_2$, —NR$_2$, —NRC(=O)R, —NRC(=O)O $(C_{1-6})$alkyl, —NRC(=O)NR$_2$, —NRC(=NR)NR$_2$, —NRSO$_2$R, —OR, —O(C$_{1-6}$)haloalkyl, —OC(=O)R, —OC(=O)O(C$_{1-6}$)alkyl, —OC(=O)NR$_2$, —SR, —S(O)R, —SO$_2$R, —OSO$_2$(C$_{1-6}$)alkyl, —SO$_2$NR$_2$, —(C$_{1-6}$)alkylene-CN, —(C$_{1-6}$)alkylene-C(=O)OR, —(C$_{1-6}$)alkylene-C(=O)NR$_2$, —(C$_{1-6}$)alkylene-OR, —(C$_{1-6}$)alkylene-OC(=O)R, —(C$_{1-6}$)alkylene-NR$_2$, —(C$_{1-6}$)alkylene-NRC(=O)R, —NR(C$_{1-6}$)alkylene-C(=O)OR, —NR(C$_{1-6}$)alkylene-C(=O)NR$_2$, —NR(C$_{2-6}$)alkylene-OR, —NR(C$_{2-6}$)alkylene-OC(=O)R, —NR(C$_{2-6}$)alkylene-NR$_2$, —NR(C$_{2-6}$)alkylene-NRC(=O)R, —O(C$_{1-6}$)alkylene-C(=O)OR, —O(C$_{1-6}$)alkylene-C(=O)NR$_2$, —O(C$_{2-6}$)alkylene-OR, —O(C$_{2-6}$)alkylene-OC(=O)R, —O(C$_{2-6}$)alkylene-NR$_2$ and —O(C$_{2-6}$)alkylene-NRC(=O)R, wherein each R group is hydrogen or (C$_{1-6}$ alkyl).

The terms "heteroaryl" or "heteroaromatic" as used herein refer to an aromatic ring system having at least one heteroatom in at least one ring, and from 2 to 9 carbon atoms in the ring system. The heteroaryl group has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaryls include furyl, thienyl, pyridyl, oxazolyl, pyrrolyl, indolyl, quinolinyl or isoquinolinyl, and the like. The heteroatoms of the heteroaryl ring system can include heteroatoms selected from one or more of nitrogen, oxygen and sulfur.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heteroaryls include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,5-naphthyridinyl, 1,8-naphthyridinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6- and 7-benzothienyl, benzoxazolyl, benzthiazolyl, purinyl, benzimidazolyl, and benztriazolyl.

A heteroaryl group can be unsubstituted or substituted. A substituted heteroaryl group can be substituted with one or more groups, e.g., 1, 2 or 3 groups, including: (C$_{1-6}$)alkyl, (C$_{2-6}$)alkenyl, (C$_{2-6}$)alkynyl, halogen, (C$_{1-6}$)haloalkyl, —CN, —NO$_2$, —C(=O)R, —C(=O)OR, —C(=O)NR$_2$, —C(=NR)NR$_2$, —NR$_2$, —NRC(=O)R, —NRC(=O)O(C$_{1-6}$)alkyl, —NRC(=O)NR$_2$, —NRC(=NR)NR$_2$, —NRSO$_2$R, —OR, —O(C$_{1-6}$)haloalkyl, —OC(=O)R, —OC(=O)O(C$_{1-6}$)alkyl, —OC(=O)NR$_2$, —SR, —S(O)R, —SO$_2$R, —OSO$_2$(C$_{1-6}$)alkyl, —SO$_2$NR$_2$, —(C$_{1-6}$)alkylene-CN, —(C$_{1-6}$)alkylene-C(=O)OR, —(C$_{1-6}$)alkylene-C(=O)NR$_2$, —(C$_{1-6}$)alkylene-OR, —(C$_{1-6}$)alkylene-OC(=O)R, —(C$_{1-6}$)alkylene-NR$_2$, —(C$_{1-6}$)alkylene-NRC(=O)R, —NR(C$_{1-6}$)alkylene-C(=O)OR, —NR(C$_{1-6}$)alkylene-C(=O)NR$_2$, —NR(C$_{2-6}$)alkylene-OR, —NR(C$_{2-6}$)alkylene-OC(=O)R, —NR(C$_{2-6}$)alkylene-NR$_2$, —NR(C$_{2-6}$)alkylene-NRC(=O)R, —O(C$_{1-6}$)alkylene-C(=O)OR, —O(C$_{1-6}$)alkylene-C(=O)NR$_2$, —O(C$_{2-6}$)alkylene-OR, —O(C$_{2-6}$)alkylene-OC(=O)R, —O(C$_{2-6}$)alkylene-NR$_2$ and —O(C$_{2-6}$)alkylene-NRC(=O)R, wherein each R group is hydrogen or (C$_{1-6}$ alkyl).

The aforementioned listing of heteroaryl moieties is intended to be representative and not limiting.

The term "nanoparticle" as used herein refers to a particle having a size from about 1 nm to about 1000 nm.

The term "nanoparticle size" as used herein refers to the median size in a distribution of nanoparticles. The median size is determined from the average linear dimension of individual nanoparticles, for example, the diameter of a spherical nanoparticle. Size may be determined by any number of methods in the art, including dynamic light scattering (DLS) and transmission electron microscopy (TEM) techniques. In some embodiments, the nanoparticle has a size from about 5 to about 1000 nm, 5 to about 500 nm, from about 5 to about 200 nm, and/or from about 5 to about 100 nm.

The term "protecting group" refers to a chemical functional group that can be used to derivatize a reactive functional group present in a molecule to prevent undesired reactions from occurring under particular sets of reaction conditions but which is capable of being introduced and removed selectively under known reaction conditions. The chemistry and use of functional groups is familiar to one skilled in the art. Discussion of protecting groups can be found, e.g., in *Protecting Group Chemistry*, 1$^{st}$ Ed., Oxford University Press, 2000; *March's Advanced Organic chemistry: Reactions, Mechanisms, and Structure*, 5$^{th}$ Ed., Wiley Interscience Publication, 2001; Peturssion, S. et al., "*Protecting Groups in Carbohydrate Chemistry,*" *J. Chem. Educ.*, 1997, 74(11), 1297, Wuts et al., *Protective Groups in Organic Synthesis*, 4$^{th}$ Ed., Wiley Interscience (2007).

The term "substituted" means that an atom or group of atoms formally replaces hydrogen as a "substituent" attached to another group. The term "substituted", unless otherwise indicated, refers to any level of substitution, namely mono-, di-, tri-, tetra- or penta-substitution, where such substitution is permitted. The substituents are independently selected, and substitution may be at any chemically accessible position. When groups are described herein as being substituted, the substituents can include, but are not limited to, (C$_{1-6}$)alkyl, (C$_{2-6}$)alkenyl, (C$_{2-6}$)alkynyl, halogen, (C$_{1-6}$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —((C$_{1-6}$)alkylene)Ar, —O((C$_{1-6}$)alkylene)Ar, —OC(=O)(C$_{1-6}$)alkyl, —OC(=O)O(C$_{1-6}$)alkyl, —OC(=O)NR$_2$, —NR$_2$, —NRAr, —NR((C$_{1-6}$)alkylene), —NRC(=O)R, —NRC(=O)Ar, —NRC(=O)O(C$_{1-6}$)alkyl, —NRC(=O)NR$_2$, —NRSO$_2$R, —SR, —S(O)R, —SO$_2$R, —OSO$_2$(C$_{1-6}$)alkyl, —SO$_2$NR$_2$, (C$_{1-8}$)perfluoroalkyl, —(C$_{2-6}$)alkylene-OR, —O(C$_2$-C$_6$)alkylene-N((C$_{1-6}$)alkyl)$_2$, —P(=O)(OR)$_2$, —OP(=O)(OR)$_2$, wherein each R group is hydrogen or (C$_{1-6}$ alkyl), e.g., methyl and wherein each Ar is independently unsubstituted aryl or heteroaryl or aryl or heteroaryl substituted with one or more of (C$_{1-6}$)alkyl, (C$_{2-6}$)alkenyl, (C$_{2-6}$)alkynyl, halogen, (C$_{1-6}$)haloalkyl, —CN, —NO$_2$, —C(=O)R, —C(=O)OR, —C(=O)NR$_2$, —C(=NR)NR$_2$, —OR, —OC(=O)(C$_{1-6}$)alkyl, —OC(=O)O(C$_{1-6}$)alkyl, —OC(=O)NR$_2$, —NR$_2$, —NRC(=O)R, —NRC(=O)O(C$_{1-6}$)alkyl, —NRC(=O)NR$_2$, —NRSO$_2$R, —SR, —S(O)R, —SO$_2$R, —OSO$_2$(C$_{1-6}$)alkyl, —SO$_2$NR$_2$, (C$_{1-8}$)perfluoroalkyl, —(C$_{2-6}$)alkylene-OR, —O(C$_{2-6}$)alkylene-N((C$_{1-6}$)alkyl)$_2$, —P(=O)(OR)$_2$, —OP(=O)(OR)$_2$ wherein each R group is hydrogen or (C$_{1-6}$ alkyl).

The term "salt" includes any ionic form of a polymer and one or more counterionic species (cations and/or anions). Salts also include zwitterionic polymers (i.e., a molecule containing one more cationic and anionic species, e.g., zwitterionic amino acids). Counter ions present in a salt can include any cationic, anionic, or zwitterionic species. Exemplary anions include, but are not limited to, chloride, bromide, iodide, nitrate, sulfate, bisulfate, sulfite, bisulfate, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethansulfonate, ethanesulfonate, benzenesulfonate, p-toluenesulfonate, p-trifluoromethylbenzenesulfonate, hydroxide, aluminates and borates. Exemplary cations include, but are not limited to, monovalent alkali metal cations, such as lithium, sodium, potassium and cesium, and divalent alkaline earth metals, such as beryllium, magnesium, calcium, strontium and barium. Also included are transition metal cations, such as gold, silver, copper and zinc, as well as nonmetal cations, such as ammonium salts. Representative organic amines useful for the formation of base addition salts include ethylamine, diethylamine, ethylenediamine, ethanolamine, diethanolamine, piperazine, and the like.

References to a polymer described and disclosed herein are considered to include the free acid, the free base, and all addition salts and complexes of the polymer. The polymers may also form inner salts or zwitterions when a free carboxy and a basic amino group are present concurrently. The term "pharmaceutically acceptable salt" refers to salts which possess toxicity profiles within a range that affords utility in pharmaceutical applications. Preparation and selection of suitable salt forms is described in Stahl et al., *Handbook of Pharmaceutical Salts: Properties, Selection, and Use*, Wiley-VCH 2002.

When in the solid state, the polymers described herein and salts thereof may occur in various forms and may, e.g., take the form of solvates, including hydrates. In general, the useful properties of the polymers described herein do not depend on whether the polymer or salt thereof is or is in a particular solid state form, such as a polymorph or solvate, so unless clearly indicated otherwise reference in the specification to polymers and salts should be understood as encompassing any solid state form of the polymer, whether or not this is explicitly stated.

Polymers provided herein can also include all isotopes of atoms occurring in the intermediates or final polymers. Isotopes include those atoms having the same atomic number but different mass numbers. For example, isotopes of hydrogen include tritium and deuterium.

The phrase "pharmaceutically acceptable" is employed herein to refer to those polymers, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The following abbreviations may be used herein: AcOH (acetic acid); Ag (silver); AgNO$_3$ (silver nitrate); aq. (aqueous); atm. (atmosphere(s)); Da (dalton(s)); dd (doublet of doublets); DCM (dichloromethane); DIPEA (N,N-diisopropylethylamine); DiI (1,1'-dioctadecyl-3,3,3',3'-tetramethylindocarbocyanine perchlorate (or another salt thereof)); DiR (1,1'-dioctadecyl-3,3,3',3'-tetramethylindotricarbocyanine Iodide) DMF (N,N-dimethylformamide); DLS (dynamic light scattering); DMEM (Dulbecco's Modified Eagle Medium); DMSO (dimethylsulfoxide); DSC (differential scanning calorimetry); DSPE-PEG 1,2-distearoyl-sn-glycero-3-phosphoethanolamine-poly(ethylene glycol); DTT (dithiothreitol); Dtxl (docetaxel); Et (ethyl); Et$_3$N or TEA (triethylamine); EtOAc (ethyl acetate); EtOH (ethanol); FBS (fetal bovine serum); FeCl$_2$ (iron (ii) chloride); g (gram(s)); GPC (gel permeation chromatography); GSH (glutathione); h (hour(s)); HPLC (high performance liquid chromatography); Li (lithium); M (molar); Me (methyl); MeCN (acetonitrile); MeOH (methanol); mg (milligram(s)); min. (minute (s)); mL (milliliter(s)); mmol (millimole(s)); mV (millivolt (s)); MRI (magnetic resonance imaging); M$_n$ or MW (molecular weight); N (normal); nm (nanometer); nM (nanomolar); NMR (nuclear magnetic resonance spectroscopy); NP (nanoparticle); NPs (nanoparticles); nPn (n-pentyl); nPr (n-propyl); PBS (phosphate-buffered saline); PDSA (poly (disulfide amide)); PEG (polyethylene glycol); PLGA (poly lactic (co-glycolic) acid); PVA (polyvinyl alcohol); rpm (revolutions per minute); s (second(s)); t-Bu (tert-butyl); TEA (triethylamine); TCEP (tris(2-carboxyethyl)phosphine; TEM (transmission electron microscopy); T$_g$ (glass transition temperature); TFA (trifluoroacetic acid); THF (tetrahydrofuran); (microgram(s)); μL (microliter(s)); μm (micromolar); wt (weight); wt % (weight percent).

II. Nanoparticle Drug Delivery System with pH Triggered Drug Release

To provide a suitable nanoparticle drug delivery system, the present disclosure provides an environment-responsive drug delivery platform comprised of hybrid polymeric NPs which can efficiently encapsulate therapeutic proteins, and yet maintain small NP size. These NPs are designed to elicit a secondary response when the pH of their surrounding environment changes from acidic to neutral/or basic, which occurs when the NPs cross over from the acidic gastrointestinal environment to the blood stream.

These NPs are made by blending at least one pH responsive polymer into at least one non-pH responsive polymer that can typically form NPs by itself without mixing with the pH-responsive polymer. The non-pH-responsive polymer aids in the formation of NPs, whereas the pH-responsive polymer imparts pH-responsiveness to the NP.

The NPs are formed (e.g., by nanoprecipitation) at a pH in which the pH-responsive polymer is insoluble. This aids in the self-assembly of the NP. As the results show, the pH during NP formation can be optimized to increase the drug loading and possibly also the degree of pH-responsiveness. The ratio of the two polymer components can be changed to optimize loading and NP size. When the NPs thus formed are exposed to a pH at which the pH-responsive polymer dissolves, it triggers a change in the NP where the drug payload is rapidly released. Although our experimental results in the specific embodiment discussed below show pH-triggered release of insulin, any surface conjugated targeting ligands can be released in a similar pH-triggered manner, especially when the targeting ligand (or any other molecule that is desired to be released when pH changes) is covalently conjugated to the pH-responsive polymer.

The NP may partially or completely dissolve when exposed to pH at which the pH-responsive polymer is soluble. Alternatively, the NP may swell and become more porous, thereby increasing the release rate.

For an example of a specific embodiment of the above polymer system, acrylate and/or methacrylate based pH-responsive polymers can be used along with non-pH responsive polymers like poly(lactic-co-glycolic acid)-poly(ethylene glycol) (PLGA-PEG) or poly(Lactic acid)-poly(ethylene glycol) (PLA-PEG).

In this study we have used Eudragit (S100 and L100) as the pH responsive polymer, and blended it with PLGA-PEG to make NPs with insulin as the payload for oral delivery. Insulin is an example of a therapeutic biologic molecule, which has to be administered to patients suffering from Type 1 diabetes. This invention, however, is broadly applicable, for example, for NPs that use a transcytosis pathway that has previously been identified called the FcRn pathway, when the NPs are decorated with Fc fragments that target them to FcRn receptors.

Surface conjugation of targeting ligands is well-known in the literature, and many different methods are available for conjugating different molecules to the surface of NPs.

The application of this platform can be extended from oral delivery to any system, where a secondary response due to a change in the pH of the environment (acidic to neutral/basic) is beneficial. Further, this pH responsive characteristic of the NPs can be extended to other large protein molecule systems and other kinds of payloads (such as small molecule drugs) and other transport pathways including intracellular pathways that involve change of pH.

Ins-Eud-PEGA-PEG NPs were designed to release insulin when triggered by a change in pH from acidic to neutral. This property of the NPs can be utilized to enable oral delivery of insulin using the FcRn pathway. where the NPs remain intact in the stomach (pH 2-3). upper small intestine (pH 5-6) and in the cellular endosomes (pH 5) where the pH is acidic but on coming in contact with blood (pH 7.4), Eudragit S100 begins to dissolve and the NP loses its integrity, resulting in rapid release of insulin.

These NPs were made using the nanoprecipitation method. Insulin. Eudragit and PLGA-PEG were mixed in an organic solvent. dimethyl sulfoxide (DMSO) and added dropwise to a beaker containing a buffer solution, which was being continuously stirred. The NP size was characterized using the dynamic light scattering (DLS) instrument and the insulin loading was measured using the BCA assay.

The NP characteristics can be optimized to overcome the challenges associated with designing efficient NPs for oral delivery of insulin. In order to find the optimum conditions for forming Ins-Eud-PLGA-PEG NPs with high loading, small size and maximum pH responsiveness, a series of experiments was performed. NPs with increasing amounts of Eudragit were prepared and the amount of insulin released in 2 h was measured. As shown in FIG. 1A, it is seen that Eudragit does not have a significant effect on insulin loading up to 10% Eudragit in the NPs. However, on increasing the Eudragit amount to 20%, a higher loading (13%) is seen, while the NP size remains small (83 nm). At amounts of Eudragit greater than 20%. the NP size increases to more than 100 nm, and at a 50% Eudragit composition, NPs with a poor size distribution, indicative of the inability to form NPs, are observed.

Figure 1B:
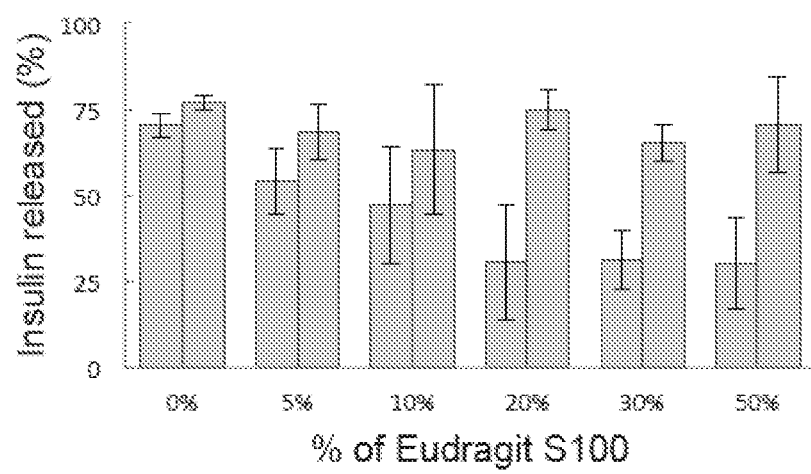
FIG. 1B is a graph showing the effect of the amount of Eudragit on pH responsiveness of the NP. pH responsiveness of the NPs increases with increasing amounts of Eudragit up to 20% Eudragit by weight.

FIG. 1B shows the effect of the amount of Eudragit on the pH responsiveness of the NP. It can be seen that decreasing amounts of insulin is released within 2 h at pH 6 as the amount of Eudragit in the NP is increased, but there is no noticeable trend in the release of insulin within 2 h at pH 7.4. However, on comparing the release of insulin in pH 6 and pH 7.4 for each composition of the NP, it can be seen that the pH responsiveness of the NPs increases as the amount of Eudragit increases in the NPs up to a Eudragit content of about 20%.

Therefore, from these experiments we can conclude that 20% Eudragit and 80% PLGA-PEG is an optimum composition of the NPs that enables maximum loading and pH responsiveness, and a particle size less than 100 nm. The NPs in these experiments were made in pH 5.

Figure 2A:
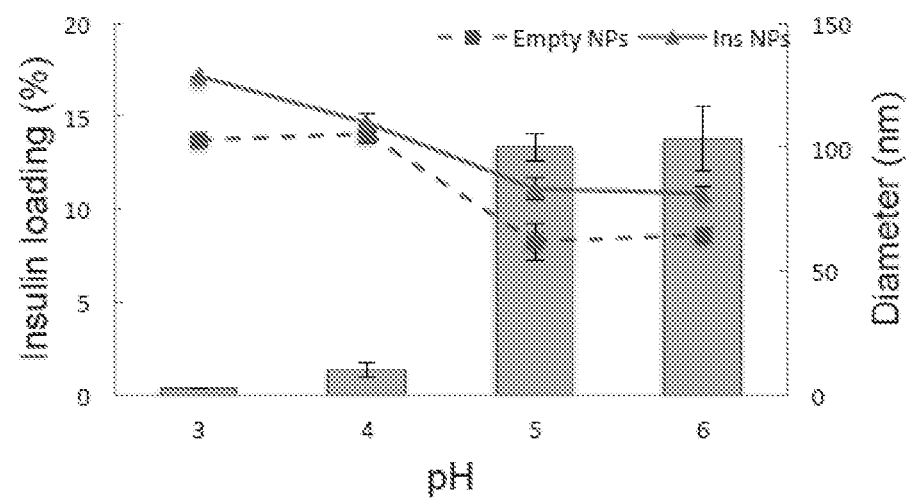
FIG. 2A is a graph showing the effect of the pH of the synthesis buffer on NP size and insulin loading. NPs with increased insulin loading and smaller size were obtained as the pH of the synthesis buffer increased.

The effect of pH of the synthesis buffer in which Ins-Eud-PLGA-PEG NPs was synthesized, on insulin loading and NP size was also investigated. Ins-Eud (20%)-PLGA-PEG (80%) NPs were synthesized in buffers at pH 3, 4, 5 and 6. The results shown in FIG. 2A demonstrate that large diameter NPs with low insulin loading were formed at pH 3 and pH 4. As the pH of the synthesizing buffer is increased to pH 5 and 6, NPs with better loading and smaller size are obtained. Since pH 6 is closer to the dissolution pH of Eudragit S 100, pH 5 was selected as the optimum pH of the synthesis buffer. Therefore, the optimum composition for the formation of the Ins-Eud-PLGA-PEG NPs is 20% Eudragit S100 and 80% PLGA-PEG and the optimum pH for synthesis is pH 5. Under these conditions the NPs have a 13% insulin loading and 83 nm diameter.

Figure 2B:
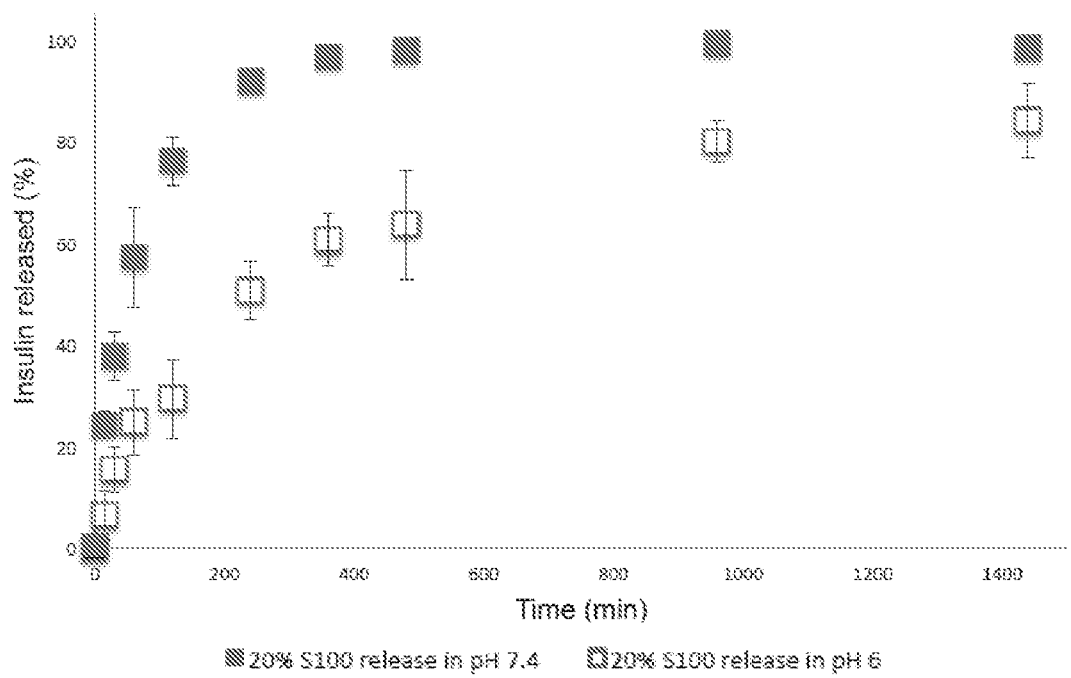
FIG. 2B is a graph showing in vitro release curve of Ins-20% Eud S100-80% PLGA-PEG NPs (Synthesis buffer: pH 5). In vitro release of insulin in pH 6 was significantly less when compared to the release of insulin in pH 7.4. The half life of insulin in pH 7.4 was 30-60 min, while the half life of insulin in pH 6 was 240 min.
Figure 3A:
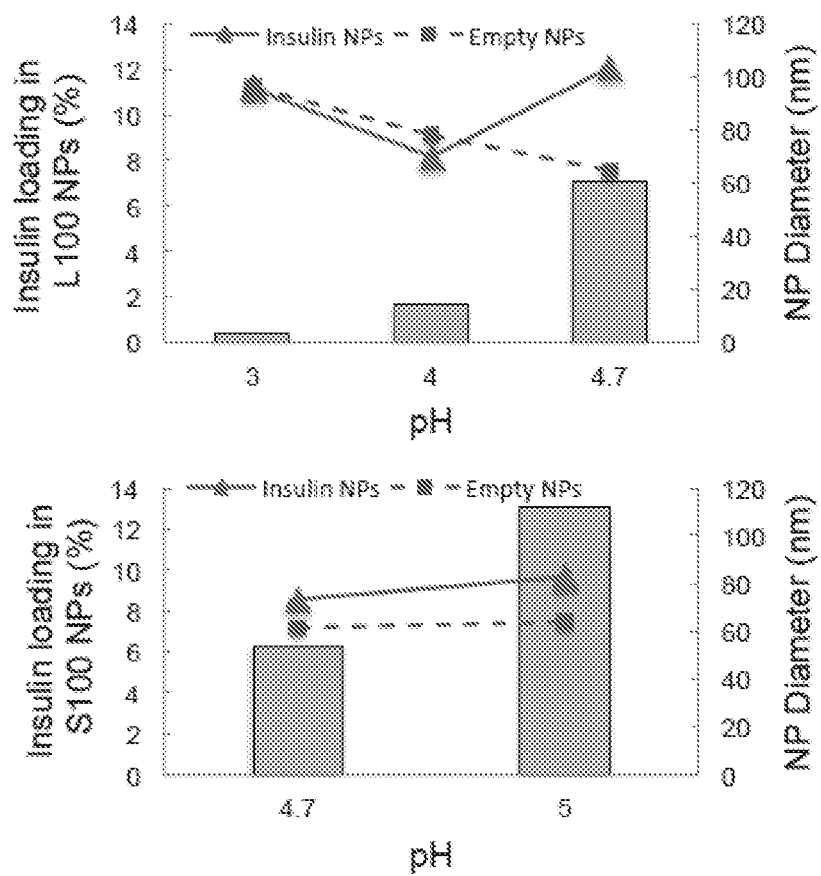
FIG. 3A is a pair of graphs showing optimization of the pH of the synthesis buffer.
Figure 3B:
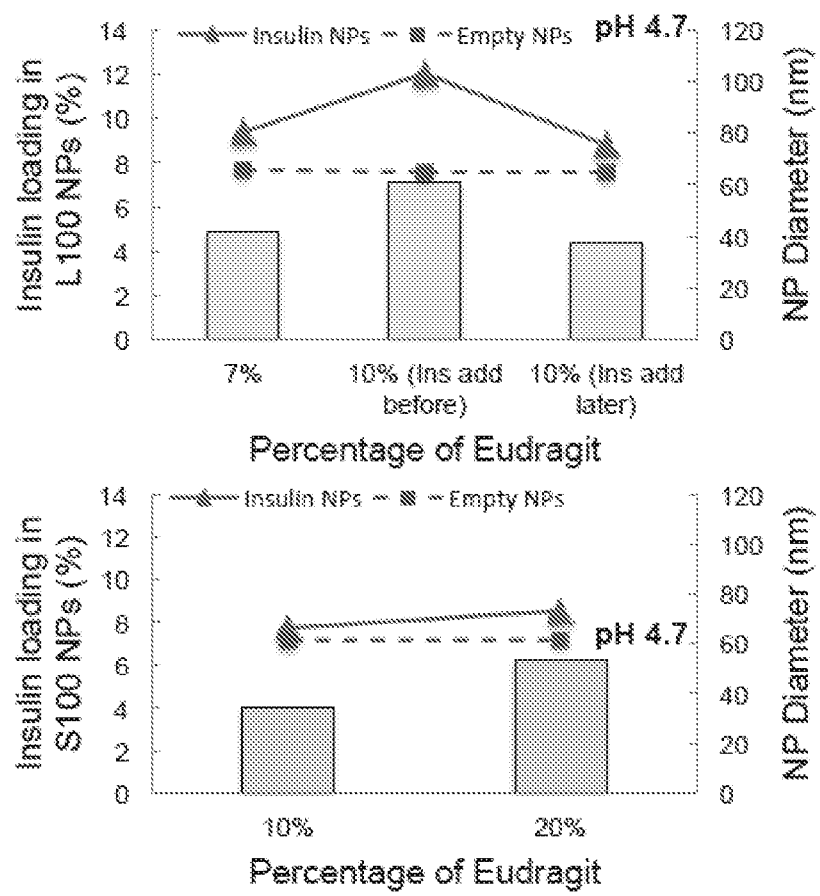
FIG. 3B is a pair of graphs showing the effects of changing amounts of Eudragit on insulin loading in the NPs.
Figure 4:
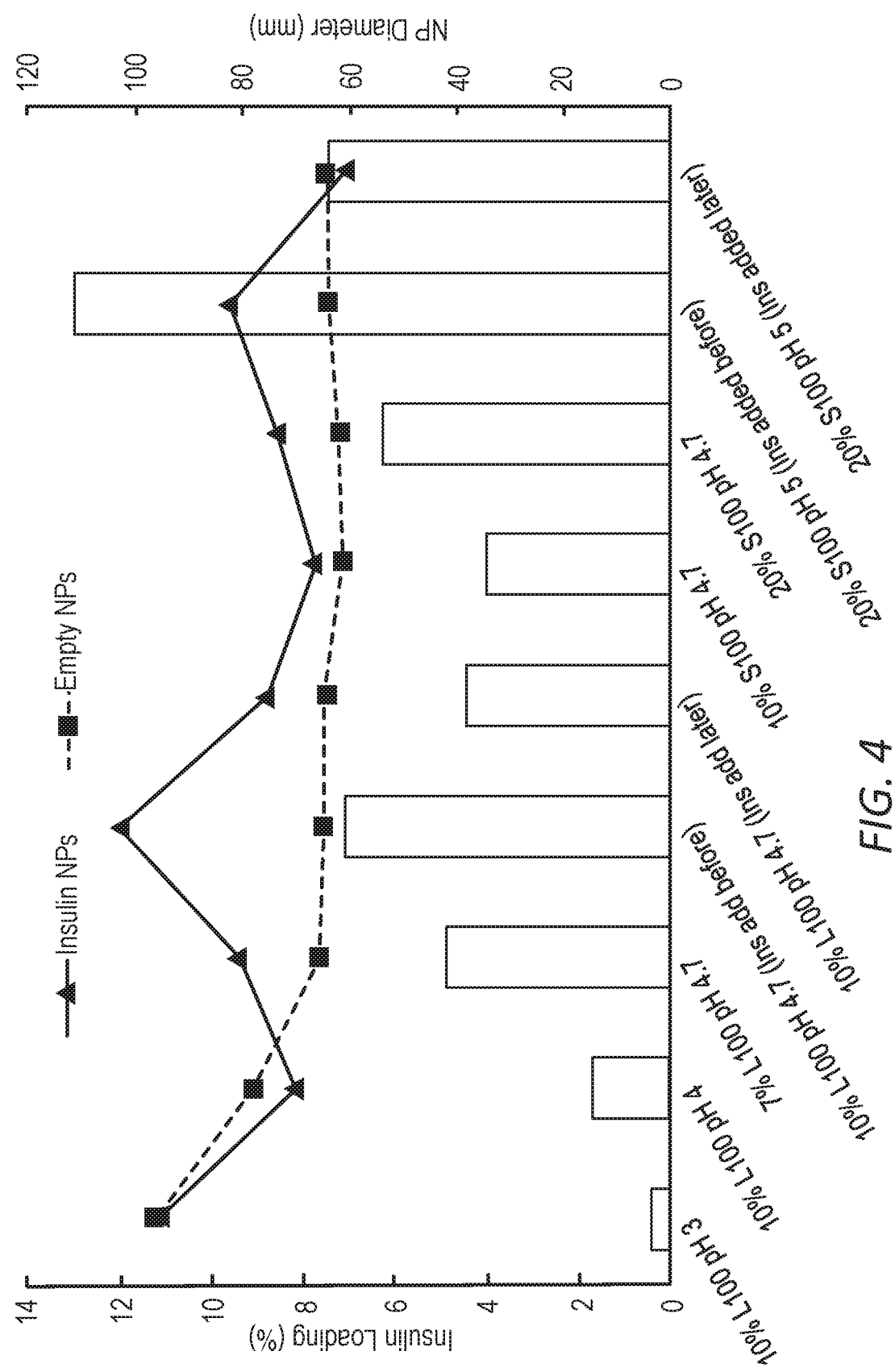
FIG. 4 is a graph showing the results of assays to screen various conditions for small NP size and high insulin loading.

FIG. 2B shows the in vitro release of 20% FudragitNPs which were synthesized in pH 5. FIG. 2B shows that there is a significant reduction in the rate at which insulin is released from the NPs at pH 6 as compared to pH 7.4. The half-life of insulin at pH 7.4 is in the range 30-60 min, while the half-life of insulin at pH 6 is 240 min.

Therefore, these NPs are designed to remain intact and prevent the loss and degradation of insulin in the stomach (pH 1-3) and in the upper intestine (pH 5-6) and trigger quick release of insulin once the NPs reach the blood (pH 7.4).

The crossover of the NPs from the upper intestinal area, through the intestinal lining can be achieved via the FcRn pathway. An Fc antibody can conjugated on the corona of the NPs. The corresponding receptor for the Fc antibody, called the FcRn attaches with the Fc at pH less than 6.5. The FeRn receptor facilitates the transcytosis of the NPs across the intestinal epithelium to and reach blood. Once the NPs reach pH 7.4 in the blood, the interaction between the Fc and the FeRn weakens, thereby releasing the NP in the blood. At this point, insulin is released and acts to regulate the level of blood glucose.

A pH-responsive nanoparticle drug delivery system as described herein has the following advantages:

i. Blending of pH-responsive and non-pH-responsive polymers to form NPs allows the creation of NPs that have small size, good polydispersity. high loading, and pJ{-responsiveness.

ii. The nanoparticles exhibit higher payload loading as compared to existing systems with the similar sizes.

iii. The nanoparticles small NP size, which is advantageous for using various transcytosis pathways.

iv. The system exhibits strong pH responsiveness. The half-life of insulin at pH 6 is 240 min, while the half-life of insulin at pH 7.4 ranges from 30-60 min.

v. These improved properties make the NPs described herein ideal candidates of oral delivery of biologics like insulin using the FeRn transcytosis pathway (in which a NP size of less than about 100 nm is preferred).

vi. These NPs and the technique to optimize NP characteristics can be extended to other biologics and applications where a pH response is desired.

The nanoparticle system described herein has significant industrial applicability. It can enable the development of a platform for the oral delivery of therapeutics, particularly biologic therapeutics such as insulin. A pill, which can be taken orally, can help replace injections, which are currently used to deliver biologics such as insulin. This drug delivery platform can be extend to many other biologics, transcytosis pathways and can be used in other systems, which require a secondary response due to a change in the environmental pH from acidic to neutral/basic.

The nanoparticle system include a nanoparticle comprising a pH-responsive polymer, a pH-insensitive polymer and a payload molecule.

In some embodiments, the pH-responsive polymer is blended with the pH-insensitive polymer forming a mixture of the polymers.

In some embodiments, the pH-insensitive polymer is a water-insoluble polymer, the aqueous solubility of which does not substantially vary with pH.

In some embodiments, the pH-insensitive polymer is a hydrophobic polymer. The pH-insensitive polymer is selected from the group consisting of polylactic acid (PLA), polypropylene oxide, poly(lactide-co-glycolide) (PLGA), poly(lactide-co-glycolide)polyethylene glycol copolymer (PLGA-PEG), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, a polymer of any of the following: methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole) and styrenes, and combinations thereof.

In some embodiments, the pH-insensitive polymer is poly(lactide-co-glycolide)polyethylene glycol copolymer (PLGA-PEG).

In some embodiments, the pH-sensitive polymer is a polymer, the aqueous solubility of which varies from being substantially insoluble to being substantially soluble with changes in pH.

In some embodiments, the pH-sensitive polymer is a polymer containing acidic groups.

In some embodiments, the pH-sensitive polymer is a polymer containing carboxylic acid groups.

In some embodiments, the aqueous solubility of the pH-sensitive polymer varies from being substantially insoluble at acidic pH to being substantially soluble at basic pH.

In some embodiments, the pH-sensitive polymer is a polymer containing basic groups.

In some embodiments, the pH-sensitive polymer is a polymer containing amine groups.

In some embodiments, the pH-sensitive polymer is a polymer containing amino groups (NH2), alkylamine groups, and/or dialkylamine groups.

In some embodiments, the aqueous solubility of the pH-sensitive polymer varies from being substantially insoluble at basic pH to being substantially soluble at acidic pH.

In some embodiments, the pH-sensitive polymer is selected from the group consisting of polyacrylic acid, polymethacrylic acid, copolymers of acrylic acid and acrylates or methacrylates, and copolymers of methacrylic acid and acrylates or methacrylates.

In some embodiments, the pH-sensitive polymer is selected from the group consisting of acrylic acid-isooctyl acrylate copolymer; ammonio methacrylate copolymer O; ammonio methacrylate copolymer type A O; ammonio methacrylate copolymer type B O; dimethylaminoethyl methacrylate-butyl methacrylate-methyl methacrylate copolymer O; methacrylic acid-ethyl acrylate copolymer (1:1) type A O; methacrylic acid-methyl methacrylate copolymer (1:1) O; methacrylic acid-methyl methacrylate copolymer (1:2) O; methacrylic acid copolymer O; methacrylic acid copolymer type A O; methacrylic acid copolymer type B O; methacrylic acid copolymer type C O; aminoalkylacrylates, aminoalkylmethacrylates, aminoalkyl(meth)acrylamides).

In some embodiments, the pH-sensitive polymer is a methacrylic acid methyl methacrylate copolymer.

In some embodiments, the pH-sensitive polymer is selected from the group consisting of methacrylic acid-methyl methacrylate copolymer (1:1) and methacrylic acid-methyl methacrylate copolymer (1:2).

In some embodiments, the pH-sensitive polymer is selected from the group consisting of EUDRAGIT® L100 and EUDRAGIT® S100.

Other polymers that can be used as the pH-sensitive or pH-insensitive polymer, as appropriate, or that can be used as additional polymeric ingredients in the nanoparticles include homopolymers (i.e., synthesized from hydrophobic monomers (e.g., styrene, methyl methacrylate, glycidyl methacrylate, DL-lactide, and the like)), random copolymers (i.e., synthesized from two or more monomers (e.g., styrene, methyl methacrylate, glycidyl methacrylate, DL-lactide, acrylic acid, methacrylic acid, 2-hydroxyethyl acrylate, and the like)), block polymers (i.e., synthesized from two or more monomers (e.g., styrene, methyl methacrylate, glycidyl methacrylate, DL-lactide, acrylic acid, methacrylic acid, 2-hydroxyethyl acrylate, and the like)), graft polymers (e.g., synthesized from artificial polymers (polyacrylic acid, polyglycidyl methacrylate, and the like) and/or natural polymers (e.g., dextran, starch, chitosan, and the like) with functional pendent groups (e.g., amino, carboxylate, hydroxyl, epoxy groups, and the like)), and/or branched polymers (e.g., a hyperbranched polyester with multifunctional alcohol building block and 2,2-bis(methylol)propionic acid branching units, such as Boltorn™ H40).

Other suitable polymers include polymer systems that are approved for use in humans, e.g., poly(glycolic acid), poly(lactic acid), poly(caprolactone), poly(lactide-co-glycolide), poly(ortho ester) II, poly(alkyl cyanoacrylate), desaminotyrosyl octyl ester, polyphosphoesters, polyester amides, polyurethanes, and lipids. Other non-limiting examples of polymers that the core can comprise include: chitosan; acrylates copolymer; acrylic acid-isooctyl acrylate copolymer; ammonio methacrylate copolymer; ammonio methacrylate copolymer type A; ammonio methacrylate copolymer type B; butyl ester of vinyl methyl ether/maleic anhydride copolymer (125,000 molecular weight); carbomer homopolymer type A (allyl pentaerythritol crosslinked); carbomer homopolymer type B (allyl sucrose crosslinked); cellulosic polymers; dimethylaminoethyl methacrylate-butyl methacrylate-methyl methacrylate copolymer; dimethylsiloxane/methylvinylsiloxane copolymer; divinylbenzene styrene copolymer; ethyl acrylate-methacrylic acid copolymer; ethyl acrylate and methyl methacrylate copolymer (2:1; 750,000 molecular weight); ethylene vinyl acetate copolymer; ethylene-propylene copolymer; ethylene-vinyl acetate copolymer (28% vinyl acetate); glycerin polymer solution i-137; glycerin polymer solution im-137; hydrogel polymer; ink/polyethylene terephthalate/aluminum/polyethylene/sodium polymethacrylate/ethylene vinyl acetate copolymer; isooctyl acrylate/acrylamide/vinyl acetate copolymer; Kollidon® VA 64 polymer; methacrylic acid-ethyl acrylate copolymer (1:1) type A; methacrylic acid-methyl methacrylate copolymer (1:1); methacrylic acid-methyl methacrylate copolymer (1:2); methacrylic acid copolymer; methacrylic acid copolymer type A; methacrylic acid copolymer type B; methacrylic acid copolymer type C; octadecene-1/maleic acid copolymer; PEG-22 methyl ether/dodecyl glycol copolymer; PEG-45/dodecyl glycol copolymer; Polyester polyamine copolymer; poly(ethylene glycol) 1,000; poly(ethylene glycol) 1,450; poly(ethylene glycol) 1,500; poly(ethylene glycol) 1,540; poly(ethylene glycol) 200; poly(ethylene glycol) 20,000; poly(ethylene glycol) 200,000; poly(ethylene glycol) 2,000,000; poly(ethylene glycol) 300; poly(ethylene glycol) 300-1,600; poly(ethylene glycol) 300-1,600; poly(ethylene glycol) 3,350; poly(ethylene glycol) 3,500; poly(ethylene glycol) 400; poly(ethylene glycol) 4,000; poly(ethylene glycol) 4,500; poly(ethylene glycol) 540; poly(ethylene glycol) 600; poly(ethylene glycol) 6,000; poly(ethylene glycol) 7,000; poly(ethylene glycol) 7,000,000; poly(ethylene glycol) 800; poly(ethylene glycol) 8,000; poly(ethylene glycol) 900; polyvinyl chloride-polyvinyl acetate copolymer; povidone acrylate copolymer; povidone/eicosene copolymer; polyoxy(methyl-1,2-ethanediyl), alpha-hydro-omega-hydroxy-, polymer with 1,1'-methylenebis[4-isocyanatocyclohexane] copolymer; polyvinyl methyl ether/maleic acid copolymer; styrene/isoprene/styrene block copolymer; vinyl acetate-crotonic acid copolymer; {poly[(9,9-di-n-octylfluorenyl-2,7-diyl)-alt-(benzo[2,1,3]thiadiazol-4,8-diyl)]}, and {poly[2,6-(4,4-bis-(2-ethylhexyl)-4H-cyclopenta [2,1-b;3,4-b']dithiophene)-alt-4,7(2,1,3-benzothiadiazole)]}.

In some embodiments, the ratio of the amount of the pH-sensitive polymer to the amount of pH-insensitive polymer is in the range from about 1:99 to about 50:50 by weight.

In some embodiments, the ratio of the amount of the pH-sensitive polymer to the amount of pH-insensitive polymer is in the range from about 1:99 to about 30:70 by weight.

In some embodiments, the ratio of the amount of the pH-sensitive polymer to the amount of pH-insensitive polymer is in the range from about 1:99 to about 20:80 by weight.

In some embodiments, the ratio of the amount of the pH-sensitive polymer to the amount of pH-insensitive polymer is in the range from about 5:95 to about 20:80 by weight.

In some embodiments, the ratio of the amount of the pH-sensitive polymer to the amount of pH-insensitive polymer is in the range from about 10:90 to about 20:80 by weight.

In some embodiments, the size of the nanoparticle is in the range from about 5 nm to about 500 nm.

In some embodiments, the size of the nanoparticle is in the range from about 5 nm to about 200 nm.

In some embodiments, the size of the nanoparticle is in the range from about 10 nm to about 100 nm.

In some embodiments, the size of the nanoparticle is in the range from about 20 nm to about 100 nm.

The size of the nanoparticles described herein can be about 1 nm to about 1000 nm. In some embodiments, the size is in the range from about 5 nm to about 1000 nm, from about 5 nm to about 500 nm, from about 5 nm to about 400 nm, from about 5 nm to about 300 nm, from about 5 nm to about 200 nm, from about 5 nm to about 100 nm, from about 20 nm to about 200 nm, from about 40 nm to about 200 nm, from about 60 nm to about 200 nm, from about 20 nm to about 180 nm, from about 40 nm to about 180 nm, from about 60 nm to about 180 nm, from about 20 nm to about 160 nm, from about 40 nm to about 160 nm, from about 60 nm to about 160 nm, and/or from about 75 nm to about 150 nm.

In some embodiments, the nanoparticles present within a population, e.g., in a composition, can have substantially the same shape and/or size (i.e., they are "monodisperse"). For example, the particles can have a distribution such that no more than about 5% or about 10% of the nanoparticles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the nanoparticles.

In some embodiments, the diameter of no more than 25% of the nanoparticles varies from the mean nanoparticle diameter by more than 150%, 100%, 75%, 50%, 25%, 20%, 10%, or 5% of the mean nanoparticle diameter. It is often desirable to produce a population of nanoparticles that is relatively uniform in terms of size, shape, and/or composition so that most of the nanoparticles have similar properties. For example, at least 80%, at least 90%, or at least 95% of the nanoparticles produced using the methods described herein can have a diameter or greatest dimension that falls within 5%, 10%, or 20% of the average diameter or greatest dimension. In some embodiments, a population of nanoparticles can be heterogeneous with respect to size, shape, and/or composition. In this regard, see, e.g., WO 2007/150030, which is incorporated herein by reference in its entirety.

Biocompatibility

The nanoparticles described herein are biodegradable and/or biocompatible, i.e., a nanoparticle containing polymers that do not typically induce an adverse response when inserted or injected into a living subject, for example, without significant inflammation and/or acute rejection of the polymers by the immune system, for instance, via a T-cell response. One test to determine biocompatibility is to expose polymers to cells in vitro, where biocompatible polymers typically do not result in significant cell death at moderate concentrations, e.g., at concentrations of about 50 µg/106 cells. For example, a biocompatible polymer may cause less than about 20% cell death when exposed to cells such as fibroblasts or epithelial cells, even if phagocytosed or otherwise taken-up by such cells. In some embodiments, the nanoparticle has an anticancer effect. In some embodiments, the nanoparticle can result in significant cell death of cancer cells without an adverse response in normal cells.

The polymers present in the nanoparticles can also be biodegradable, i.e., the polymers are able to degrade, chemically and/or biologically, within a physiological environment, such as within the body. Degradation of the polymers can occur at varying rates, depending on the polymers or copolymers used. For example, the half-life of the polymers (the time at which 50% of the polymers are degraded into monomers and/or other nonpolymeric moieties) can be on the order of days, weeks, months, or years, depending on the particular polymers used to make the nanoparticles. The polymers can be biologically degraded, e.g., by enzymatic activity in cleavage of amide bonds present or cellular machinery, in some cases, for example, through exposure to the reductive environment of a cell to degrade the —S—S— bonds. In some cases, the polymers can be broken down into monomers and/or other nonpolymeric moieties that cells can either reuse or dispose of without significant toxic effect on the cells (e.g., polymer can be hydrolyzed to form cysteine).

Methods of Making the Nanoparticles

The methods of forming the nanoparticles allow for a uniform synthesis, which affords a uniform size and shape of the resulting nanoparticles. One advantage of the invention allows for the simple and rapid synthesis of nanoparticles by a nanoprecipitation method. In one aspect, a method for preparing a nanoparticle of the disclosure comprises (a) dissolving a pH sensitive polymer and a pH-insensitive polymer polar aprotic solvent to give a polymer solution; and (b) adding the polymer solution to water to provide the nanoparticle. For example, the polymer solution can be added dropwise to water to facilitate the nanoprecipitation process. In some embodiments, the polar aprotic solvent is DMSO. In some embodiments, the concentration of the polymers in the polymer solution is in the range from about 0.5 to about 100 mg/mL. In some embodiments, the concentration of the polymers in the polymer solution is in the range from about 1 to about 30 mg/mL. In some embodiments, the concentration of the polymer in the polymer solution is in the range from about 5 to about 10 mg/mL. A payload also dissolved in the polymer solution, and subsequently is incorporated into the nanoparticle.

Compositions

Also provided is a composition comprising nanoparticle containing a payload as described herein. The composition may comprise a nanoparticle as described herein, using a method of synthesizing the nanoparticle described above. In some embodiments, the polymers making up the nanoparticle are not covalently attached to the payload. For example, in some embodiments, the polymers encapsulate the payload. In some embodiments, the payload is covalently attached to one of the polymers. For example, the polymer can be covalently attached to a drug molecule via a linker.

Payload

The methods and compositions described herein are useful for delivering a payload. In some embodiments, the payload is delivered to a biological target. The payload can be used, e.g., for labeling (e.g., a detectable agent such as a fluorophore), or for therapeutic purposes (e.g., a cytotoxin or other drug molecule).

The proportion of the payload relative to the polymers used in the composition depends on the characteristics of the payload, the properties of the polymers, and the application. In some embodiments, the payload is loaded in the range from about 0.01% by weight to about 100.0% by weight compared with the weight of the polymers. The payload can be in the range from about 1% by weight to about 80% by weight, from about 1% by weight to about 75% by weight, from about 1% by weight to about 70% by weight, from about 1% by weight to about 65% by weight, from about 1% by weight to about 60% by weight, from about 1% by weight to about 55% by weight, from about 1% by weight to about 50% by weight, from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight compared with the weight of the polymers.

Drug Molecules

Drug molecules include small molecules and biomolecules. Small molecules are low molecular weight organic compounds (typically less than about 2000 daltons). In some embodiments, the molecular weight of the drug molecule is in the range from about 300 to about 2000, from about 300 to about 1800, from about 300 to about 1600, from about 300 to about 1400, from about 300 to about 1200, from about 300 to about 1000, from about 300 to about 800, and/or from about 300 to about 600 daltons. Examples include cytochalasin B, gramicidin D, ethidium bromide, emetine, mitomycin, etoposide, tenoposide, colchicin, daunorubicin, dihydroxy anthracin dione, mithramycin, actinomycin D, 1-dehydrotestosterone, glucocorticoids, procaine, tetracaine, lidocaine, amphotericin B, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Non-limiting examples of compositions of the present disclosure with a drug molecule payload are shown in FIGS. 5I-5O.

Other drug molecules include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), antifungal agents (e.g., butenafine, terbinafine, and naftifine), immunomodulating drugs (e.g., glatiramer acetate, fingolimod, teriflunomide, and dimethyl fumarate), and anti-mitotic agents (e.g., vincristine, vinblastine, paclitaxel, and maytansinoids).

Examples of suitable chemotherapeutic agents include any of: abarelix, aldesleukin, alitretinoin, allopurinol, altretamine, anastrozole, arsenic trioxide, asparaginase, azacitidine, bexarotene, bleomycin, bortezomib, busulfan, calusterone, capecitabine, carboplatin, carmustine, chlorambucil, cisplatin, cladribine, clofarabine, cyclophosphamide, cytarabine, dacarbazine, dactinomycin, dalteparin, dasatinib, daunorubicin, decitabine, denileukin, dexrazoxane, docetaxel, doxorubicin, dromostanolone, epirubicin, erlotinib, estramustine, etoposide, exemestane, filgrastim, floxuridine, fludarabine, fluorouracil, fulvestrant, gefitinib, gemcitabine, goserelin acetate, histrelin acetate, idarubicin, ifosfamide, imatinib, irinotecan, lapatinib ditosylate, lenalidomide, letrozole, leucovorin, leuprolide, levamisole, lomustine, meclorethamine, megestrol, melphalan, mercaptopurine, methotrexate, methoxsalen, mitomycin C, mitotane, mitoxantrone, nandrolone, nelarabine, nofetumomab, oxaliplatin, paclitaxel, pamidronate, pegaspargase, pegfilgrastim, pemetrexed, pentostatin, pipobroman, plicamycin, procarbazine, quinacrine, rasburicase, ruxolitinib, sorafenib, streptozocin, sunitinib, tamoxifen, temozolomide, teniposide, testolactone, thalidomide, thioguanine, thiotepa, topotecan, toremifene, tretinoin, uracil mustard, valrubicin, vinblastine, vincristine, vinorelbine, vorinostat, and zoledronate, or a pharmaceutically acceptable salt thereof.

Small molecules useful in the compositions and methods described herein bind with high affinity to a biopolymer, such as protein, nucleic acid, or polysaccharide, or other biological target. In one aspect, useful small molecules are capable of being functionalized by condensation with a carboxylic acid. For example, a small molecule can be an agent such as paclitaxel, which binds specifically to microtubules and is capable of being functionalized, e.g., with a carboxylic acid for attachment as an ester via a linker to the pH-sensitive or pH-insensitive polymer. Other examples include small molecules that bind specifically to receptors for hormones, cytokines, chemokines, or other signaling molecules, that may be encapsulated by the nanoparticles. Small molecules include peptides.

The term "linker" as used herein refers to a group of atoms, e.g., 0-500, 0-10,000 atoms, and may be comprised of the atoms or groups such as, but not limited to, carbon, amino, alkylamino, oxygen, sulfur, sulfoxide, sulfonyl, carbonyl, and imine. The linker chain may also comprise part of a saturated, unsaturated or aromatic ring, including polycyclic and heteroaromatic rings wherein the heteroaromatic ring is an aryl group containing from one to four heteroatoms, N, O or S. Specific examples include, but are not limited to, unsaturated alkanes, polyethylene glycols, and dextran polymers. The linker must not interfere with binding of the ligand to the target.

In its simplest form, a linker can be a covalent chemical bond. In other embodiments, the linker can be a chemical group. Since the function of the linking group is merely to provide a physical connection, a wide variety of chemical groups can serve as linking groups. A linker is typically a divalent organic linking group where one valency represents the point of attachment to ligand or payload molecule and one valency represents the attachment to the polymer. The only requirement for the linker is to provide a stable physical linkage that is compatible with maintaining the function of the ligand or payload molecule and is compatible with the chemistry.

Examples of suitable linking groups include, e.g.: —O—, —S—, —S(O)—, —S(O)$_2$—, —C(O)—, —NH—, —N(C$_{1-6}$)alkyl, —NHC(O)—, —C(O)NH—, —O(CO)—, —C(O)O—, —O(CO)NH—, —NHC(O)O—, —O(CO)O—, —NHC(O)NH—, —O(C$_{1-6}$)alkylene-, —S(C$_{1-6}$)alkylene-, —S(O)(C$_{1-6}$)alkylene-, —S(O)$_2$(C$_{1-6}$)alkylene-, —C(O)(C$_{1-6}$)alkylene-, —NH((C$_{1-6}$)alkylene)C(O)—, —C(O)((C$_{1-6}$)alkylene)C(O)—, —C(O)((C$_{1-6}$)alkylene)NH—, —O(CO)—, —C(O)O—, —O(CO)NH—, —NHC(O)O—, —O(CO)O—, —NHC(O)NH—, unsubstituted-(C$_{1-10}$)alkylene-, unsubstituted-(C$_{1-10}$)heteroalkylene, or —(C$_{1-10}$)alkylene or —(C$_{1-10}$)heteroalkylene substituted with one or more (e.g., 1, 2, 3, 4 or 5 substituents) independently selected from the group consisting of (C$_{1-6}$)alkyl, (C$_{2-6}$)alkenyl, (C$_{2-6}$)alkynyl, halogen, (C$_{1-6}$)haloalkyl, —CN, —NO$_2$, —C(=O)R, —OC(=O)Ar, —C(=O)OR, —C(=O)NR$_2$, —C(=NR)NR$_2$, —OR, —Ar, —OAr, —((C$_{1-6}$)alkylene)Ar, —O((C$_{1-6}$)alkylene)Ar, —OC(=O)(C$_{1-6}$)alkyl, —OC(=O)O(C$_{1-6}$)alkyl, —OC(=O)NR$_2$, —NR$_2$, —NRAr, —NR((C$_{1-6}$)alkylene)Ar, —NRC(=O)R, —NRC(=O)Ar, —NRC(=O)O(C$_{1-6}$)alkyl, —NRC(=O)NR$_2$, —NRSO$_2$R, —SR, —S(O)R, —SO$_2$R, —OSO$_2$(C$_{1-6}$)alkyl, —SO$_2$NR$_2$, (C$_{1-8}$)perfluoroalkyl, —(C$_{2-6}$)alkylene-OR, —O(C$_{2-6}$)alkylene-N((C$_{1-6}$)alkyl)$_2$, —P(=O)(OR)$_2$, —OP(=O)(OR)$_2$, oxo and sulfido, wherein each R group is hydrogen or (C$_{1-6}$ alkyl), e.g., methyl and wherein each Ar is independently unsubstituted aryl or heteroaryl or aryl or heteroaryl substituted with one or more of (C$_{1-6}$)alkyl, (C$_{2-6}$)alkenyl, (C$_{2-6}$)alkynyl, halogen, (C$_{1-6}$)haloalkyl, —CN, —NO$_2$, —C(=O)R, —C(=O)OR, —C(=O)NR$_2$, —C(=NR)NR$_2$, —OR, —OC(=O)(C$_{1-6}$)alkyl, —OC(=O)O(C$_1$-C$_6$)alkyl, —OC(=O)NR$_2$, —NR$_2$, —NRC(=O)R, —NRC(=O)O(C$_{1-6}$)alkyl, —NRC(=O)NR$_2$, —NRSO$_2$R, —SR, —S(O)R, —SO$_2$R, —OSO$_2$(C$_1$-C$_6$)alkyl, —SO$_2$NR$_2$, (C$_{1-8}$)perfluoroalkyl, —(C$_{2-6}$)alkylene-OR, —O(C$_{2-6}$)alkylene-N((C$_{1-6}$)alkyl)$_2$, —P(=O)(OR)$_2$, —OP(=O)(OR)$_2$ wherein each R group is hydrogen or (C$_{1-6}$ alkyl). In addition, —(C$_{1-10}$)alkylene- and —(C$_{1-10}$)heteroalkylene can be substituted by one or more oxo groups (C=O) and the nitrogen and sulfur atoms of a heteroalkylene group can optionally be oxidized (e.g., to form S(O), —S(O)$_2$—, or N-oxide). Suitable heteroalkylene groups can include one or more 1,2-dioxyethylene units —(O—CH$_2$CH$_2$)$_n$O—, where n is an integer, e.g., 1, 2, 3, 4 or 5). The —(C$_{1-10}$)alkylene- and —(C$_{1-10}$)heteroalkylene also include —(C$_{1-6}$)alkylene- and —(C$_{1-6}$)heteroalkylene; and —(C$_{1-3}$)alkylene- and —(C$_{1-3}$)heteroalkylene.

Biomolecules

Biomolecules are organic molecules having a molecular weight of 200 daltons or more produced by living organisms or cells, including large polymeric molecules such as polypeptides, proteins, polysaccharides, polynucleotides and nucleic acids (e.g., DNA or RNA, such as siRNA, mRNA, or shRNA), or analogs or derivatives of such molecules.

In some embodiments, the biomolecule comprises a nucleic acid. For example, the nucleic acid can be selected from the group consisting of siRNAs, microRNAs, mRNAs, and DNAs. The nucleic acid may be double-stranded (e.g., double-stranded DNA) or single-stranded (e.g., single-stranded RNA). The nucleic acid can comprise a vector (e.g., a plasmid or a viral vector, e.g., one derived from a retrovirus, a lentivirus, an adenovirus, or an adeno-associated virus). In some embodiments, the nucleic acid can reduce expression of a protein (e.g., a protein associated with a disease state, e.g., a kinase upregulated in a cancer, such as BRAF-mutated melanoma). In some embodiments, the nucleic acid can introduce or enhance expression of a protein (e.g., to encode for a protein that is depleted in a disease state, e.g., normal CFTR protein to treat cystic fibrosis).

In some embodiments, the siRNA is siMYC (i.e., anti-MYC siRNA). In some embodiments, the siRNA is si-c-MYC (i.e., anti-c-MYC siRNA). In some embodiments, the siRNA is siBRAF (i.e., anti-BRAF siRNA). In some embodiments, the siRNA is siBRAF$^{V600E}$ (i.e., anti-BRAF$^{V600E}$ siRNA).

In some embodiments, the biomolecule comprises a therapeutic protein, such as an antibody, a transmembrane protein, a growth factor, an enzyme, or a structural protein. Examples that can be used in any embodiment of the disclosed compositions include cytokines, such as transforming growth factor-beta (TGF-beta), interferons (e.g., interferon-alpha, interferon-beta, interferon-gamma), colony stimulating factors (e.g., granulocyte colony stimulating factor (GM-CSF)), thymic stromal lymphopoietin (TSLP), and the interleukins, e.g., interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35; polypeptide hormones, such as amylin, anti-Müllerian hormone, calcitonin, cholecystokinin, corticotropin, endothelin, enkephalin, erythropoietin (EPO), follicle-stimulating hormone, gallanin, gastrin, ghrelin, glucagon, gonadotropin-releasing hormone, growth hormone-releasing hormone, hepcidin, human chorionic gonadotropin, human growth hormone (hGH), inhibin, insulin, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, and vasopressin; antibody-drug conjugates (e.g., trastuzumab emtansine, brentuximab vedotin, T-DM1); antibody fragment-drug conjugates; protein-drug conjugates; peptide-drug conjugates (e.g., paclitaxel-Angiopep 2, BMTP-11 (Arrowhead Research), zoptarelin doxorubicin, and NGR-hTNF); fusion proteins (i.e., a chimeric protein formed by the expression of two or more genes that encode for different proteins), e.g., Fc fusion proteins, which contain an antibody Fc unit that can offer stability or selective targeting of a cell or tissue type, including therapeutic proteins, such as ataci-cept, abatacept, aflibercept, alefacept, belatacept, etanercept, sotatercept, romiplostim, and rilonacept, bispecific fusion proteins (i.e., bispecific antibodies), which comprise two arms from different antibodies, and are thereby able to target two different types of antigens, such as Ec-LDP-Hr-AE, MM-111 (Merrimack Pharmaceuticals), and IMCgp100 (Immunocore Ltd.), and multimeric fusion proteins, which are fusion proteins created by engineered multimerization (e.g., with streptavidin or using leucine zippers), such as polyvalent IgG2a Fc (M045); enzymes, e.g., agalsidase beta, imiglucerase, velaglucerase alfa, taliglucerase, alglucosidase alfa, laronidase, idursulfase, and galsulfase; and antibodies, including therapeutic antibodies, e.g., anticancer antibodies (e.g., abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, zalutumumab), and anti-inflammatory antibodies (e.g., adalimumab, alemtuzumab, atlizumab, canakinumab, certolizumab, certolizumab pegol, daclizumab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, and briakinumab). Further examples of useful therapeutic proteins can be found in U.S. Pat. Nos. 8,349,910; and 8,043,833; U.S. patent applications 2013/0195888; and 2007/0092486; and PCT WO 2014/130064, each of which is hereby incorporated by reference in its entirety. In some embodiments, biomolecules can be sensitive to physiological environments, e.g., to physiologic enzymes or local pH, before delivery to the target tissue or target cell.

In some embodiments, a payload consists essentially of, or consist of, one or more species as described herein.

Detectable Agents

Examples of detectable agents include various organic small molecules, inorganic compounds, nanoparticles, enzymes or enzyme substrates, fluorescent materials, luminescent materials, bioluminescent materials, chemiluminescent materials, radioactive materials, and contrast agents. Examples of suitable enzymes include horseradish peroxidase, alkaline phosphatase, β-galactosidase, or acetylcholinesterase; examples of suitable fluorescent materials include boron-dipyrromethene (BODIPY®), 4,4-difluoro-5,7-dimethyl-4-bora-3a,4a-diaza-s-indacene-3-propionic acid (BODIPY® FL), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X), Oregon Green 88, 6-(((4,4-difluoro-5-(2-pyrrolyl)-pyrrolyl)-4-bora-3a,4a-diaza-s-indacene-3-yl)styryloxy)acetyl)aminohexanoic acid, Nile red (9-diethylamino-5-benzo[α]phenoxazinone), succinimidyl ester (BODIPY® 650/665-X), 7-N,N-diethylaminocoumarin, VIVOTAG 680 (an amine-reactive near-infra-red fluorochrome, from VisEn Medical), umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, or $^{3}$H, $^{99m}$Tc (e.g., as pertechnetate (technetate(VII), TcO$_4$) either directly or indirectly, or other radioisotope detectable by direct counting of radioemission or by scintillation counting. In some embodiments, the molecular weight of the detectable agent is in the range from about 300 to about 2000, from about 300 to about 1000, and/or from about 300 to about 600 daltons. In addition, contrast agents, e.g., contrast agents for MRI or NMR, for X-ray CT, Raman imaging, optical coherence tomography, absorption imaging, ultrasound imaging, or thermal imaging can be used. Exemplary contrast agents include gold, gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons. In some embodiments, the detectable agent comprises gadolinium.

For example, a composition of the present disclosure may be used to deliver a payload of chelated Gd (e.g., Gd-DTPA) to a cancer tumor for MRI imaging. The payload may allow for greater uptake of the payload and imaging of, e.g., different areas within a cancer tumor, since the uptake of the composition would not be mediated by passive transport. A composition of the present disclosure may be taken up via active transport mechanisms (e.g., phagocytosis, pinocytosis) and thus may avoid issues of Pgp efflux, commonly exhibited by cancer cells, that would limit uptake of the chelated Gd.

Controlled Release

The compositions of the disclosure can provide for controlled release or sustained release of a payload (e.g., a biomolecule) in a biological system, e.g., when a biomolecule is delivered to a subject in need of therapy. Controlled release refers to delivery of an agent at a controlled rate for an extended time or in response to a stimulus (e.g., upon a change in pH or temperature, or in the presence of an enzyme). Controlled release of a payload can provides a well-characterized and reproducible dosage form. Sustained release refers to the release of a payload over an extended period of time. In sustained release, the rate and duration of payload release can be controlled to achieve a particular profile. A sustained release profile can include zero-order release, exponential decay, step-function release, or other release profiles that carry over a period of time, e.g., one to several hours (e.g., about 8 hours or 24 hours), one to several days (e.g., about 2, 3, 4, 5, 6, 7, 10, or 14 days), one to several weeks (e.g., about 2, 3, or 4 weeks) or one to several months (e.g., about 2, 3, 4, 5, or 6 months). The terms "zero-order release", "exponential decay" and "step-function release" as well as other sustained release profiles are well known in the art.

The nanoparticles described herein can provide for release in the manner that depends on pH of the environment to which the nanoparticles are exposed. The nanoparticles can be tuned to release the payload at a particular pH by varying the amount and acid or base properties of the pH-sensitive polymer. While not being limited by any theory, it is understood that the nanoparticles described herein will begin to release the payload at an enhanced rate when the pH exceeds the pKa of an acidic pH-sensitive polymer included in the nanoparticle, or when the pH is less than the pKa of a basic pH-sensitive polymer included in the nanoparticle.

The controlled release profiles can afford enhanced pharmacokinetic profiles of a payload within a subject, compared with a naked payload that has not been loaded into a particle of the disclosure. An enhanced pharmacokinetic profile can exhibit an improved property of one or more selected from AUC, half-life, clearance, mean residence time, and volume of distribution (Vss), and can be shown in a given subject and route of administration as described herein. In some embodiments, the AUC of a payload in a particle of the disclosure is in a range from about 100% to about 100,000%, from about 100% to about 1000%, from about 150% to about 700%, or from about 200% to about 500% of the AUC of a naked payload, or wherein the AUC of the payload in the particle is about 150%, about 200%, about 250%, about 300%, about 350%, about 400%, about 450%, about 500%, or greater than 500% of the AUC of a naked payload. In some embodiments, the half-life of a payload in a particle of the disclosure is in a range from about 100% to about 100,000%, from about 100% to about 1000%, from about 100% to about 500%, from about 150% to about 400%, or from about 200% to about 300% of the half-life of a naked payload, or wherein the half-life of the payload in the particle is about 150%, about 200%, about 250%, about 300%, or greater than 400% of the half-life of a naked payload. In some embodiments, the clearance of a payload in a particle of the disclosure is in a range from about 1% to about 100%, from about 10% to about 90%, from about 20% to about 80%, from about 30% to about 70%, or from about 40% to about 80% of the clearance of a naked payload, or wherein the clearance of the payload in the particle is about 3%, about 5%, about 10%, about 15%, about 20%, about 25%, about 30%, about 40%, about 50%, about 60%, about 70%, or about 80% of the clearance of a naked payload. In some embodiments, the mean residence time of a payload in a particle of the disclosure is in a range from about 100% to about 100,000%, from about 100% to about 1000%, from about 150% to about 700%, or from about 200% to about 500% of the mean residence time of a naked payload, or wherein the mean residence time of the payload in the particle is about 150%, about 200%, about 250%, about 300%, about 350%, about 400%, about 450%, about 500%, or greater than 500% of the mean residence time of a naked payload.

Formulations

Stabilizers

Figure 5:
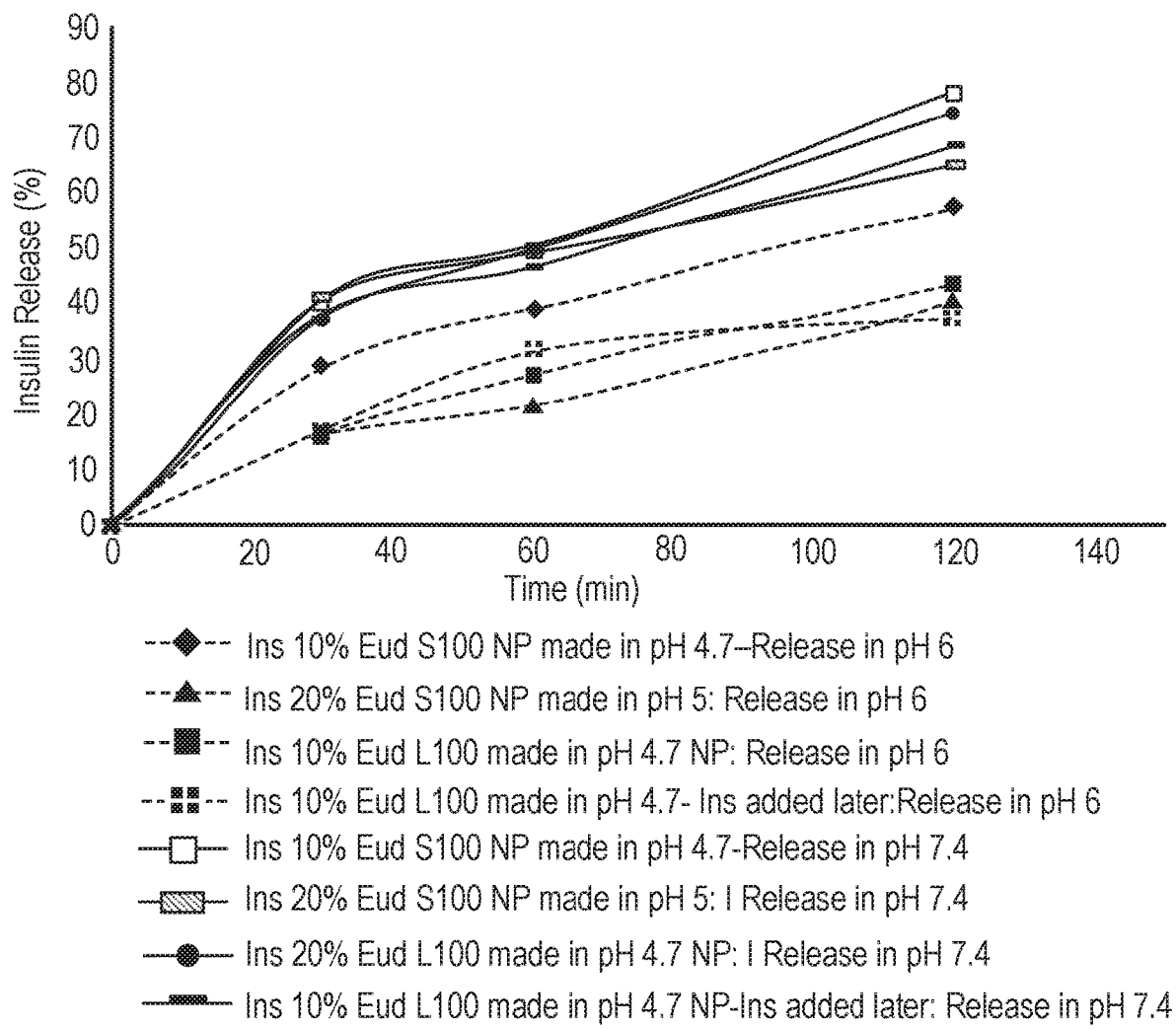
FIG. 5 is a graph showing the results of assays screening for maximum pH responsiveness.
Figure 6:
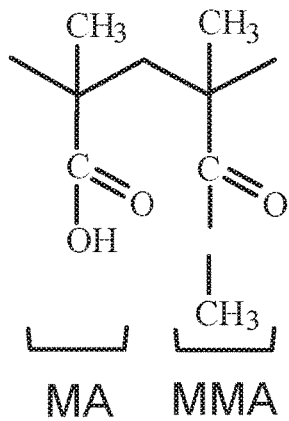
FIG. 6 is an illustration of the structure of eudragit S100 and L100.
Figure 7:
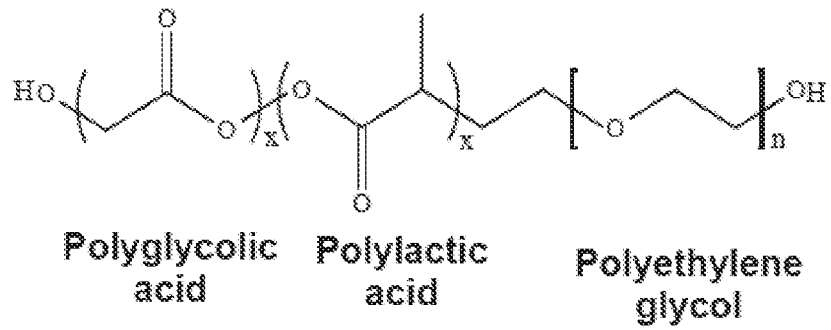
FIG. 7 is an illustration of the structure of Block copolymer $PLGA_{10K}$-$PEG_{5K}$.
Figure 8:
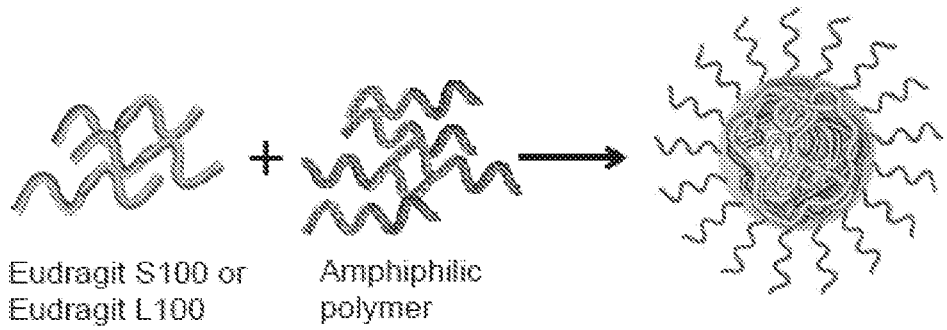
FIG. 8 is a schematic illustration of the components of exemplary nanoparticles.
Figure 9:
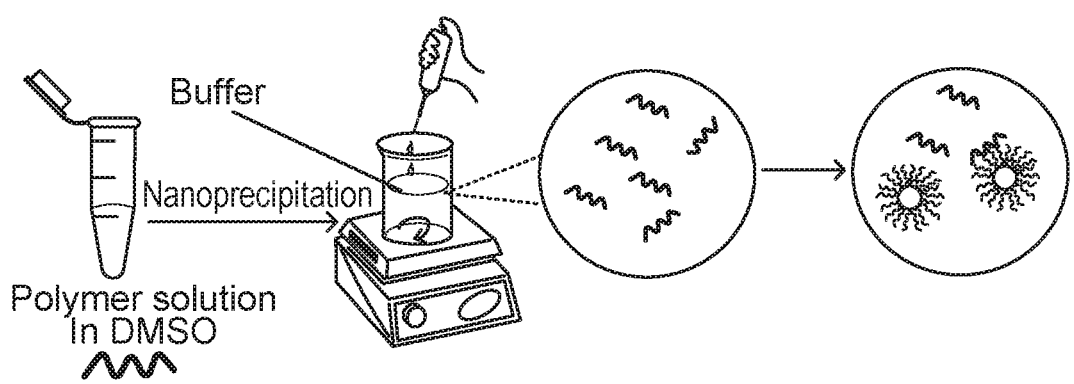
FIG. 9 is a schematic illustration of an exemplary nanoprecipitation synthesis method; see, e.g., Taluja, A. J. Mat. Chem. [1] 2007, 17, 4002-4014. This method can be followed by size measurement using dynamic light scattering and protein quantification using a BCA assay (Pratap, N. Journal of Microencapsulation, June 2008; 25(4): 248-256).

To provide additional stability, in some embodiments, a nanoparticle, or a composition of the present disclosure may be protected with a stabilizer, such as a coating, for example, PVA (MW), Tween® 80, Pluronic® (e.g., F127, F68, etc.), PEG, MYRJ™, lipid, or lipid-PEG. Specific coating stabilizers include DSPE-PEG3000/Lipid and PLGA50K/DSPE-PEG3000, and are well-known in the art. Non-limiting examples of compositions of the present disclosure with lipid coating are shown in FIGS. 5P and 5Q.

Additional Ingredients

A composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

Compositions containing nanoparticles as described herein can be administered in various forms, depending on the disease or disorder to be treated and the age, condition, and body weight of the subject, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

A tablet may be made by compression or molding, optionally with one or more accessory ingredients. Compressed tablets may also be prepared using inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

Liquid dosage forms for oral administration include pharmaceutically acceptable emulsions, microemulsions, solutions, suspensions, syrups, and elixirs. In addition to the nanoparticles, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Suspensions, in addition to the nanoparticles, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include a polymer and a drug molecule or a detectable agent as provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, NJ). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prolonged absorption of the injectable compositions can be brought about by including in the composition an agent that delays absorption, for example, aluminum monostearate and gelatin.

Sterile injectable solutions can be prepared by incorporating the nanoparticles in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation is freeze-drying (lyophilization), which yields a powder of the active ingredient plus any additional desired ingredient from a previously sterile-filtered solution thereof.

For administration by inhalation, the nanoparticles can be delivered in the form of an aerosol spray from a pressured container or dispenser that contains a suitable propellant, e.g., a gas such as carbon dioxide, or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998).

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (polysorbates, e.g., TWEEN®; poloxamers, e.g., PLURONIC®; sorbitan esters; lecithin; and polyethoxylates, e.g., CREMOPHOR®), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Systemic administration of a composition as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compositions are formulated into ointments, salves, gels, or creams as generally known in the art.

The ointments, pastes, creams, and gels may contain, in addition to one or more polymers provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the nanoparticles described herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration", "administered systemically", "peripheral administration", and "administered peripherally" as used herein mean the administration of a composition via route other than directly into the central nervous system, such that it enters the subject's system and thus, is subject to metabolism and other like processes, for example, subcutaneous administration.

Actual dosage levels of the active ingredients in the compositions provided herein may be varied so as to obtain an amount of the active ingredient which is effective to achieve the desired therapeutic response for a particular subject, composition, and mode of administration, without being toxic to the subject.

The concentration of a drug molecule or detectable agent provided herein in a pharmaceutically acceptable composition will vary depending on several factors, including the dosage of the compound to be administered, the pharmacokinetic characteristics of the drug molecule(s) employed, and the route of administration. In some embodiments, the compositions provided herein can be provided in an aqueous solution containing about 0.1-10% w/v of a drug molecule or detectable agent disclosed herein, among other substances, for parenteral administration. Typical dose ranges can include from about 0.01 to about 50 mg/kg of body weight per day, given in 1-4 divided doses. Each divided dose may contain the same or different drug molecules. The dosage will be a therapeutically effective amount depending on several factors including the overall health of a subject, and the formulation and route of administration of the selected drug molecule(s).

Dosage forms or compositions containing a drug molecule or detectable agent as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the subject, the nature and severity of the disorder to be treated or prevented, the route of administration and the form of the drug or agent, in general, a daily dosage of from 0.01 to 2000 mg of the compound is recommended for an adult human subject, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given subject will depend upon the activity, pharmacokinetics, and bioavailability of a particular drug molecule, physiological condition of the subject (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The compositions can be included in a container, pack, or dispenser together with instructions for administration.
Administration When employed as pharmaceuticals, the particles of the invention can be administered in the form of pharmaceutical compositions. Thus the present disclosure provides a composition comprising a particle, or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the particle of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active particle, soft and hard gelatin capsules, suppositories, sterile injectable solutions and sterile packaged powders.

In preparing a formulation, the active particle can be milled to provide the appropriate particle size prior to combining with the other ingredients. If the active particle is substantially insoluble, it can be milled to a size of less than 200 mesh. If the active particle is substantially water soluble, the size can be adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the subject by employing procedures known in the art.

In some embodiments, the pharmaceutical composition comprises silicified microcrystalline cellulose (SMCC) and at least one particle described herein, or a pharmaceutically acceptable salt thereof. In some embodiments, the silicified microcrystalline cellulose comprises about 98% microcrystalline cellulose and about 2% silicon dioxide w/w.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active particle may be effective over a wide dosage range and is generally administered in a therapeutically effective amount. It will be understood, however, that the amount of the particle actually administered will usually be determined by a physician, according to the relevant circumstances, including the condition to be treated, the chosen route of administration, the actual particle administered, the age, weight, and response of the individual subject, the severity of the subject's symptoms and the like.

The therapeutic dosage of a particle of the present invention can vary according to, e.g., the particular use for which the treatment is made, the manner of administration of the particle, the health and condition of the subject, and the judgment of the prescribing physician. The proportion or concentration of a particle of the invention in a pharmaceutical composition can vary depending upon a number of factors including dosage, chemical characteristics (e.g., hydrophobicity), and the route of administration. For example, the particles of the invention can be provided in an aqueous physiological buffer solution containing about 0.1 to about 10% w/v of the particle for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the particle selected, formulation of the excipient, and its route of administration. Effective doses can be extrapolated from dose-response curves derived from in vitro or animal model test systems.

The liquid forms in which the particles and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the particle of the invention. The topical formulations can be suitably packaged in tubes of, e.g., 100 g which are optionally associated with instructions for the treatment of the select indication, e.g., psoriasis or other skin condition.

The amount of particle or composition administered to a subject will vary depending upon what is being administered, the purpose of the administration, such as prophylaxis or therapy, the state of the subject, the manner of administration and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the particle preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a particle of the present invention can vary according to, e.g., the particular use for which the treatment is made, the manner of administration of the particle, the health and condition of the subject, and the judgment of the prescribing physician. The proportion or concentration of a particle of the invention in a pharmaceutical composition can vary depending upon a number of factors including dosage, chemical characteristics (e.g., hydrophobicity), and the route of administration. For example, the particles of the invention can be provided in an aqueous physiological buffer solution containing about 0.1 to about 10% w/v of the particle for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the particle selected, formulation of the excipient, and its route of administration. Effective doses can be extrapolated from dose-response curves derived from in vitro or animal model test systems.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:
1. A nanoparticle comprising a pH-responsive polymer blended with a pH-insensitive polymer forming a mixture of the polymers, and a payload molecule, wherein the ratio of the amount of the pH-responsive polymer to the amount of pH-insensitive polymer is in the range from 10:90 to 20:80 by weight.
2. The nanoparticle of claim 1, wherein:
the pH-insensitive polymer is selected from the group consisting of polylactic acid (PLA), polypropylene oxide, poly(lactide-co-glycolide) (PLGA), poly(lactide-co-glycolide)polyethylene glycol copolymer (PLGA-PEG), poly(epsilon-caprolactone), poly(ethylethylene), polybutadiene, polyglycolide, polymethylacrylate, polyvinylbutylether, polystyrene, polycyclopentadienyl-methylnorbornene, polyethylenepropylene, polyethylethylene, polyisobutylene, polysiloxane, a polymer of any of the following: methyl acrylate, ethyl acrylate, propyl acrylate, n-butyl acrylate, isobutyl acrylate, 2-ethyl acrylate, t-butyl acrylate, methacrylates selected from the group consisting of ethyl methacrylate, n-butyl methacrylate, isobutyl methacrylate, acrylonitriles, methacrylonitrile, vinyls selected from the group consisting of vinyl acetate, vinylversatate, vinylpropionate, vinylformamide, vinylacetamide, vinylpyridines, vinyllimidazole, styrenes, and combinations thereof; and
the pH-responsive polymer is selected from the group consisting of polyacrylic acid, polymethacrylic acid, copolymers of acrylic acid and acrylates or methacrylates, and copolymers of methacrylic acid and acrylates or methacrylates or
the pH-responsive polymer is selected from the group consisting of acrylic acid-isooctyl acrylate copolymer; ammonio methacrylate copolymer O; ammonio methacrylate copolymer type A O; ammonio methacrylate copolymer type B O; dimethylaminoethyl methacrylate-butyl methacrylate-methyl methacrylate copolymer O; methacrylic acid-ethyl acrylate copolymer (1:1) type A O; methacrylic acid-methyl methacrylate copolymer (1:1) O; methacrylic acid-methyl methacrylate copolymer (1:2) O; methacrylic acid copolymer O; methacrylic acid copolymer type A O; methacrylic acid copolymer type B O; methacrylic acid copolymer type C O; aminoalkylacrylates, aminoalkylmethacrylates, and aminoalkyl(meth)acrylamides.
3. The nanoparticle of claim 2, wherein:
the pH-insensitive polymer is poly(lactide-co-glycolide) polyethylene glycol copolymer (PLGA-PEG); and
the pH-responsive polymer is a methacrylic acid methyl methacrylate copolymer selected from the group consisting of methacrylic acid-methyl methacrylate copolymer (1:1) and methacrylic acid-methyl methacrylate copolymer (1:2).
4. The nanoparticle of claim 3, wherein the ratio of the amount of the pH-responsive polymer to the amount of pH-insensitive polymer is 20:80 by weight.
5. The nanoparticle of claim 3, wherein the size of the nanoparticle is in the range from about 10 nm to about 100 nm.
6. The nanoparticle of claim 3, wherein the size of the nanoparticle is in the range from about 20 nm to about 100 nm.
7. The nanoparticle of claim 1, wherein the payload molecule is a biomolecule.
8. The nanoparticle of claim 2, wherein the payload molecule is a biomolecule selected from the group consisting of: transforming growth factor-beta, interferons, colony stimulating factors, granulocyte colony stimulating factor (GM-CSF), thymic stromal lymphopoietin (TSLP), interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, interleukin-35, amylin, anti-Müllerian hormone, calcitonin, cholecystokinin, corticotropin, endothelin, enkephalin, erythropoietin (EPO), follicle-stimulating hormone, gallanin, gastrin, ghrelin, glucagon, gonadotropin-releasing hormone, growth hormone-releasing hormone, hepcidin, human chorionic gonadotropin, human growth hormone (hGH), inhibin, insulin, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, vasopressin, atacicept, abatacept, alefacept, etanercept, romiplostim, rilonacept, agalsidase beta, imiglucerase, velaglucerase alfa, taliglucerase, alglucosidase alfa, laronidase, idursulfase, galsulfase, abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, zalutumumab, adalimumab, alemtuzumab, atlizumab, canakinumab, certolizumab, certolizumab pegol, daclizumab, efalizumab, fontolizumab, golimumab, infliximab, mepolizumab, natalizumab, omalizumab, ruplizumab, ustekinumab, visilizumab, zanolimumab, vedolizumab, otelixizumab, teplizumab, rituximab, ocrelizumab, and briakinumab.
9. The nanoparticle of claim 7, wherein the payload molecule is insulin.
10. The nanoparticle of claim 1, wherein the payload molecule is conjugated to the pH-responsive polymer or the pH-insensitive polymer.

11. The nanoparticle of claim 1, wherein the nanoparticle further comprises a targeting molecule.

12. The nanoparticle of claim 11, wherein the targeting molecule is an antibody.

13. The nanoparticle of claim 12, wherein the targeting molecule is conjugated to the pH-responsive polymer or the pH-insensitive polymer.

14. A method of delivering a payload molecule to an individual in need thereof, comprising administering to the individual an effective amount of a nanoparticle of claim 1, that provides to the subject a therapeutically effective amount of the payload molecule.

15. A method of treating diabetes in a subject in need thereof, the method comprising administering to the subject a therapeutically effective amount of a nanoparticle of claim 1, wherein the payload molecule is indicated for treatment of diabetes.

16. The method of claim 15, wherein the payload molecule is insulin.

* * * * *

UNITED STATES PATENT AND TRADEMARK OFFICE
CERTIFICATE OF CORRECTION

PATENT NO. : 11,833,255 B2
APPLICATION NO. : 15/766706
DATED : December 5, 2023
INVENTOR(S) : Sunandini Chopra et al.

It is certified that error appears in the above-identified patent and that said Letters Patent is hereby corrected as shown below:

In the Claims

In Column 35, Lines 42-43, Claim 2, delete "vinyllimidazole," and insert -- vinylimidazole, --

In Column 36, Line 28, Claim 8, delete "gallanin," and insert -- galanin, --

In Column 36, Line 56, Claim 8, delete "totumumab" and insert -- tositumomab --

Signed and Sealed this
Thirteenth Day of February, 2024

Katherine Kelly Vidal
*Director of the United States Patent and Trademark Office*